(12) United States Patent
Brouillette et al.

(10) Patent No.: US 9,169,190 B2
(45) Date of Patent: Oct. 27, 2015

(54) METHODS FOR MAKING RETINOIDS AND USES THEREOF

(71) Applicant: The UAB Research Foundation, Birmingham, AL (US)

(72) Inventors: Wayne J. Brouillette, Pelham, AL (US); Donald D. Muccio, Hoover, AL (US); Venkatram Reddy Atigadda, Birmingham, AL (US); John M. Ruppert, Birmingham, AL (US); Susan M. Lobo Ruppert, Birmingham, AL (US)

(73) Assignee: The UAB Research Foundation, Birmingham, AL (US)

(*) Notice: Subject to any disclaimer, the term of this patent is extended or adjusted under 35 U.S.C. 154(b) by 168 days.

(21) Appl. No.: 13/856,631

(22) Filed: Apr. 4, 2013

(65) Prior Publication Data
US 2013/0317106 A1    Nov. 28, 2013

Related U.S. Application Data

(63) Continuation of application No. 11/661,030, filed as application No. PCT/US2005/029922 on Aug. 23, 2005, now abandoned.

(60) Provisional application No. 60/604,089, filed on Aug. 24, 2004.

(51) Int. Cl.
C07C 205/00    (2006.01)
C07C 229/00    (2006.01)
(Continued)

(52) U.S. Cl.
CPC ............. *C07C 57/50* (2013.01); *C07C 29/14* (2013.01); *C07C 45/29* (2013.01); *C07C 45/292* (2013.01); *C07C 45/30* (2013.01); *C07C 45/513* (2013.01); *C07C 45/61* (2013.01); *C07C 45/673* (2013.01); (Continued)

(58) Field of Classification Search
CPC ........ C07C 57/50; C07C 45/29; C07C 45/30; C07C 45/61; C07C 45/68; C07C 45/292; C07C 45/513; C07C 45/673; C07C 47/238; C07C 49/403; C07C 49/417; C07C 49/603; C07C 49/683; C07C 49/713; C07C 49/753; C07C 51/09; C07C 67/343; C07C 403/08; C07C 403/14; C07C 403/20; C07C 29/04; C07C 57/26; C07C 69/618; C07C 2101/02; C07C 2101/14; C07C 2101/16; C07C 2102/10; C07C 2102/28; C07D 311/96; C12C 11/02; C07B 2200/09
USPC .......... 514/559, 563; 562/435, 455, 469, 492, 562/510
See application file for complete search history.

(56) References Cited

U.S. PATENT DOCUMENTS 4,920,123 A    4/1990    Beyer, Jr.
5,094,783 A    3/1992    Muccio et al.
(Continued)

OTHER PUBLICATIONS

Sani, "In Chemistry and Biology of Synthetic Retinoids," Dawson, M.I., Okamuar, W.H., Eds.; CRC Press: Boca Raton, FL, pp. 365-384 (1990).
(Continued)

*Primary Examiner* — T. Victor Oh
(74) *Attorney, Agent, or Firm* — Kilpatrick Townsend & Stockton LLP

(57) ABSTRACT

Described herein are methods for making retinoids. Also described herein are retinoids and methods of use thereof.

11 Claims, 3 Drawing Sheets

(51) Int. Cl.

| | |
|---|---|
| C07C 59/40 | (2006.01) |
| C07C 63/333 | (2006.01) |
| C07C 61/00 | (2006.01) |
| A61K 31/20 | (2006.01) |
| A61K 31/195 | (2006.01) |
| C07C 57/50 | (2006.01) |
| C07C 29/14 | (2006.01) |
| C07C 45/29 | (2006.01) |
| C07C 45/30 | (2006.01) |
| C07C 45/51 | (2006.01) |
| C07C 45/61 | (2006.01) |
| C07C 45/67 | (2006.01) |
| C07C 45/68 | (2006.01) |
| C07C 47/238 | (2006.01) |
| C07C 49/403 | (2006.01) |
| C07C 49/417 | (2006.01) |
| C07C 49/603 | (2006.01) |
| C07C 49/683 | (2006.01) |
| C07C 49/713 | (2006.01) |
| C07C 49/753 | (2006.01) |
| C07C 51/09 | (2006.01) |
| C07C 67/343 | (2006.01) |
| C07C 403/08 | (2006.01) |
| C07C 403/14 | (2006.01) |
| C07C 403/20 | (2006.01) |
| C07D 311/96 | (2006.01) |
| C12C 11/02 | (2006.01) |
| C07C 57/26 | (2006.01) |

(52) U.S. Cl.
CPC ............... *C07C 45/68* (2013.01); *C07C 47/238* (2013.01); *C07C 49/403* (2013.01); *C07C 49/417* (2013.01); *C07C 49/603* (2013.01); *C07C 49/683* (2013.01); *C07C 49/713* (2013.01); *C07C 49/753* (2013.01); *C07C 51/09* (2013.01); *C07C 57/26* (2013.01); *C07C 67/343* (2013.01); *C07C 403/08* (2013.01); *C07C 403/14* (2013.01); *C07C 403/20* (2013.01); *C07D 311/96* (2013.01); *C12C 11/02* (2013.01); *C07B 2200/09* (2013.01); *C07C 2101/02* (2013.01); *C07C 2101/14* (2013.01); *C07C 2101/16* (2013.01); *C07C 2102/10* (2013.01); *C07C 2102/28* (2013.01)

(56) References Cited

U.S. PATENT DOCUMENTS

| | | | |
|---|---|---|---|
| 5,256,410 A | 10/1993 | Tanner et al. | |
| 5,661,179 A | 8/1997 | Samid | |
| 6,172,112 B1 | 1/2001 | Brouillette et al. | |

OTHER PUBLICATIONS

Suh et al., "Arzoxifene, a new selective estrogen receptor modulator for chemoprevention of experimental breast cancer," Cancer Res. 61:8412-8415 (2001).
Tiami et al., "Growth, differentiation, and death of retinoid acid-treated human acute promyelocytic leukemia NB4 cells," Exp. Cell Res. 230:69-75 (1997).
Vaezi et al., "A conformationally defined 6-s-trans retinoic acid isomer: synthesis, chemopreventive activity and toxicity," J. Med. Chem. 37: 4499-4507 (1994).
Vaezi et al., "Preparation of the 9-cis, 13-cis, and all trans-isomers of α- and β-retinal," Org. Prep. Proc. Int., 19:187-195 (1987).
Verma et al., "Vitamin A acid (retinoic, acid), a potent inhibitor of 12-O-tetradecanoyl-phorbol-13-acetate-induced ornithine decarboxylase activity in mouse epidermis," Cancer Res. 37: 2196-2201 (1977).

Yang Yen et al., "Antagonism between retinoic acid receptors and AP-1: implications for tumor promotion and inflammation," New Biol. 3:1206-1219 (1991).
Zhang et al., "Retinoid X receptor is an auxiliary protein for thyroid hormone and retinoic acid receptors," Nature 355:441-446 (1992).
Ahmad et al., "The allylic halogenation of methyl 3-methylbut-2-enoate," J. Chem. Soc. C:185-187 (1968).
Alam et al., "Conformationally defined 6-s-trans-retinoic acid analogs. 2. Selective agonists for nuclear receptor binding and transcriptional activity," J. Med. Chem., 38: 2303-2310 (1995).
Anzano et al., "Prevention of breast cancer in the rat with 9-cis-retinoic acid as a single agent and in combination with tamoxifen," Cancer Res. 54:4614-4617 (1994).
Arbusov et al., "Michaelis-Arbusow-Und Perkow-Reactionen," Pure Appl. Chem., 9:307-335 (1964).
Atigadda et al., "Conformationally defined retinoic acid analogues. 5. Large-scale synthesis and mammary cancer chemopreventive activity for (2E, 4E, 6Z, 8E)-8-(3',4'-dihydro-1'(2'H)-naphthalen-1'-ylidene)-3, 7-dimethyl-2,4,6-octatrienoic acid (9cUAB30)," J. Med. Chem., 46: 3766-3769 (2003).
Boehm et al., "Synthesis and structure-activity relationships of novel X receptor-selective retinoids," J. Med. Chem. 37:2930-2941 (1994).
Breitman et al., "Growth and differentiation of human myeloid leukemia cell line HL60," Methods Enzymol. 190:118-130 (1990).
Cambier et al., "GM-CSF hypersensitivity in CD34+ purified cells in juvenile and adult chronic myelomonocytic leukemia: Effect of retinoids," Blood 86 (Suppl. 1), 791a. (1995).
Castleberry et al., "A pilot study of isoretinoin in the treatment of juvenile chronic myelogenous leukemia," N. Engl. J. Med. 331:1680-1684 (1994).
Castleberry et al., "Preliminary experience with 13-cis retinoic acid (CRA) in the treatment of juvenile chronic myelogenous leukemia (JCML)," Blood 78 (Suppl. 1), 170a. (1991).
Chandraratna et al., "Synthesis and pharmacological activity of conformationally restricted, acetylenic retinoid analogs," BioMed. Chem. Lett. 5:523-527 (1995).
Chen et al., "Two distinct actions of retinoid-receptor ligands," Nature 382:819-822 (1996).
Degos et al., "All-trans-retinoic acid as a differentiating agent in the treatment of acute promyelocytic leukemia," Blood 85:2643-2653 (1995).
Emanuel et al., "Characterization of early response gene expression in juvenile myelomonocytic leukemia syndrome (JMML)," Blood (Suppl. 1), 728a. (1995).
Emanuel et al., "Juvenile myelomonocytic leukemia: molecular understanding and prospects for theapy," Mol. Med. Today 2:468-475 (1996).
Emanuel et al., "Selective hypersensitivity to granulocyte-macrophage colony-stimulating factor by juvenile chronic myeloid leukemia hematopoietic progenitors," Blood 77:925-929 (1991).
Emanuel et al., "The role of monocyte-derived hemopoietic growth factors in the reguation of myeloproliferation in juvenile chronic myelogenous leukemia," Exp. Hematol., 19:1017-1024 (1991).
Fanjul et al., "A new class of retinoids with selective inhibition of AP-1 inhibits proliferation," Nature 372:107-11 (1994).
Frigerio et al., "A user-friendly entry to 2-iodobenzoic acid (IBX)," J. Org. Chem. 64(12): 4537-4538 (1999).
Gedye et al., "The stereochemistry of the Reformatsky reaction of methyl 4-bromo-3-methylbut-2-enoate with β-cyclocitral and related compounds," Can. J. Chem. 53:1943-1948 (1975).
Gorman et al., "In Vitro Metabolic Characterizaton, Phenotyping, and Kinetic Studies of 9cUAB30, a Retinoid X Receptor-Specific Retinoid," Drug Metabolism and Disposition 35:1157-1164, 2007.
Graupner et al., "Dual regulatory role for thyroid-hormone receptors allows control of retinoic-acid receptor activity," Nature (London) 340:653-656 (1989).
Grubbs et al., "9cUAB30, an RXR specific retinoid, and/or tamoxifen in the prevention of methylnitrosourea-induced mammary cancers," Can. Letters 201: 17-24 (2003)
Grubbs et al., "Efficacy of new retinoids in the prevention of mammary cancers and correlations with short-term biomarkers," Carcinogen, 27(6)1232-1239 (2006).

(56) References Cited

OTHER PUBLICATIONS

Gudas, "Retinoids and vertebrate development," J. Biol. Chem. 269:15399-15402 (1994).
Hale et al., "Preparation of high specific activity all trans-α-retinyl-11-3H acetate," Labeled Compds. Radiopham. 13:123-135 (1977).
International Preliminary Report on Patentability for PCT/US05/029922 mailed Feb. 28, 2007.
International Search Report and Written Opinion for PCT/US05/029922 mailed Jun. 20, 2006.
Jiang et al., "Prevention of KLF4-mediated tumor initiation and malignant transformation by UAB30 rexinoid," Cancer Biology & Therapy 8:3, 287-296; Feb. 1, 2009.
Jonathan et al., "Treatment of former smokers with 9-cis-retinoic acid reverse loss of retinoic acid receptor-β expression in the bronchial epithelium: results from a randomized placebo-controlled trial," J. Natl. Cancer Inst. 95:206-214 (2003).
Kizaki et al., "Effects of novel retinoid X receptor-selective ligands on myeloid leukemic differentiation and proliferation in vitro," Blood 87:1977-1984 (1996).
Kizaki et al., "Novel retinoic acid, 9-cis retinoic acid, in combination with all-trans retinoic acid is an effective inducer of differentiation of retinoic acid-resistant HL-60 cells," Blood 83:3289-3297 (1994).
Kolesar et al., "A Pilot, First-in-Human, Pharmacokinetic Study of 9cUAB30 in Healthy Volunteers," Cancer Prev Res 1565-1570, 3(12) Dec. 2010.
Lake et al., "A structural model for a new class of conformationally constrained retinoid: (2Z,4E)-4[3',4'-dihydro-1'(2'H)-naphthalene-1'-ylidene]-2-butenoic acid," J. Chem. Crystallogr. 27:231-235 (1997).
Lapidot et al., "Abberrent growth properties of juvenile chronic myelogenous leukemia (JCML) CD34+ cells in vitro and in vivo using scid mouse assays," Blood 82 (Suppl. 1), 197a. (1993).
Lee et al., "Phase 1 evaluation of all-trans-retinoic acid in adults with solid tumors," J. Clin. Oncol. 11:9590966 (1993).
Lehmann et al., "Retinoids selective for retinoid x receptor response pathways," Science 1944-1946 (1992).
Lin et al., "Murine toxicology and pharmacology of UAB-8, a conformationally constrained analog of retinoic acid," Toxicol. Appl. Pharmacol. 139:310-316 (1996).
Love et al., "The Novel Retinoid, 9cUAB30, Inhibits Telomerase and Induces Apoptosis in HL60 Cells1," Translational Oncology. vol. X, No. Y. 2008, pp. 1-5.
Mangelsdorf et al., "In the Retinoids Biology, Chemistry and Medicine," 2nd ed., Raven Press: New York. pp. 319-349 (1994).
Miller et al., "Initial clinical trial of the retinoid receptor pan agonist 9-cis retinoic acid," Clin. Cancer Res. 2:471-475 (1996).
Muccio et al., "Conformationally defined 6-s-trans-retinoic acid analogs. 3. Structure-activity relationships for nuclear receptor binding, transcriptional actibity, and cancer chemopreventive activity," J. Med. Chem. 39: 3625-3635 (1995).
Muccio et al., "Conformatonally defined retinoic acid analogues. 4. Potential new agents for acute promyelocytic and juvenile myelomonocylic leukemias," J. Med. Chem. 41: 1679-1687 (1998).
Nadzan, Retinoids for the treatment of oncological diseases, Annu Rev. Med. Chem. 30:119-128 (1995).
Nagpal et al., "Separation of transactivation and AP1 antagonism functions of retinoic acid receptor α," J. Biol. Chem. 270:923-927 (1995).
National Institutes of Health, Grant No. 5 P50 CA 89919, 1995.
Pattenden et al., "Carotenoids and related compounds. Part XVIII. Synthesis of cis- and di-cis-polyenes by reactions of the Wittig type," J. Chem. Soc. C:1984-1997 (1968).
Rosen et al., "Intracellular receptors and signal transducers and activators of transcription superfamilies: Novel targets for small-molecule drug discovery," J. Med. Chem. 38:4855-4874 (1995).
Salbert et al., "Retinoic acid receptors and retinoid X receptor-α-down-regulate the transforming growth factor-β1 promotor by antagonizing AP-1 activity," Mol. Endocrinol. 7:1347-1356 (1993).
Sani et al., "Determination of binding affinities of retinoids to retinoic acid-bindin protein and serum albumin," Biochem. J. 171:711-717 (1978).

METHODS FOR MAKING RETINOIDS AND USES THEREOF

CROSS REFERENCE TO RELATED APPLICATIONS

This application claims priority to U.S. Provisional Application No. 60/604,089, filed Aug. 24, 2004, the entire disclosure of which application is hereby incorporated herein in its entirety by this reference.

ACKNOWLEDGEMENTS

The research leading to this invention was funded in part by the National Institutes of Health, Grant No. 5 P50 CA 89019. The U.S. Government may have certain rights in this invention.

BACKGROUND

Retinoid receptors and other members of this superfamily of nuclear receptors, which include the steroid, thyroid and vitamin D hormone receptors and other "orphan" receptors without known ligands, are new targets for drug development (1). It is thought that retinoic acid (RA) and synthetic retinoids act as ligand-dependent transcription factors with different members of nuclear retinoid receptors to control gene transcription responsible for cellular proliferation, differentiation, development and cell death (2). Two classes of nuclear retinoid receptors (RARs and RXRs) have been identified so far, and each has several different subtypes ($\alpha$, $\beta$, $\gamma$). Both (all-E)- and (9Z)-RA bind to RARs and activate transcription mediated by RAR/RXR heterodimers, but (9Z)-RA is the most potent retinoic acid isomer for the RXRs that mediate transcription by forming homodimers or heterodimers.

Recent advances in chemotherapy and chemoprevention have heightened interest in the use of retinoids for preventing or treating several types of cancer, and major therapeutic successes have been demonstrated with retinoids in certain leukemias (3). (all-E)-RA treatment of patients with acute promyelocytic leukemia (APL) leads to a 90% complete remission rate in these patients by inducing normal maturation and apoptosis of APL myeloblasts to neutrophils, but this differentiation therapy is transient and is commonly followed by relapse within 3-15 months, probably due to the development of resistance to retinoic acid (4). (13Z)-RA effectively controls the excessive myeloproliferation in up to 50% of children with juvenile myelomonocytic leukemia (JMML) (5). However, this treatment is not curative and at best can lead to a period of prolonged stabilization of disease, but ultimately patients need to undergo allogenic bone marrow transplantation (4, 6).

All-trans-retinoic acid (ATRA) is the first example of a FDA-approved agent used for differentiation therapy (rather than standard cytotoxic cancer chemotherapy) of patients with APL. Even though it has been shown to be highly effective in APL treatment, clinical resistance occurs frequently with pharmacological doses of ATRA and APL patients often relapse (4). In order to provide more effective therapies, new highly active retinoids need to be identified in the expectation that lower doses of these agents would not induce resistance as rapidly as ATRA.

Some of the most promising retinoids in cancer prevention are 9cRA and related analogs that bind to RXRs. When 9cRA is added to the diet of rats, the number of N-methyl-N-nitrosourea (MNU)-induced mammary cancers was reduced by 92% (30). Because of excessive toxicity, however, the usefulness of 9cRA for chemoprevention of cancer in the human is limited (31-33). To increase the therapeutic index, considerable effort has been devoted toward synthesis of RXR-selective analogs of 9cRA (34, 35). Our laboratory has described the synthesis of several such retinoids and showed that these compounds were effective for the prevention of skin tumors and had lower toxicity than natural retinoids (36). Subsequently, we reported the synthesis of 9cUAB30 which is a selective agonist for the RXRs (37). We have recently shown that this retinoid is comparable in the chemopreventive efficacy of mammary cancers to 9cRA, but it is less toxic (Atigadda et al. J. Med. Chem., 2003).

Tamoxifen, an estrogen antagonist, was the first drug approved by the Federal Drug Administration for breast cancer prevention. This agent and other selective estrogen receptor modulators (SERMs) have been evaluated as a major therapeutic modality in various stages of breast cancer (38). Anti-estrogen therapy, however, is not without risks and limitations; thus, new cancer chemopreventive agents that are effective and non-toxic are needed.

It would be desirable to produce retinoids in high yield and stereoselectivity. For example, retinoids generally possess multiple carbon-carbon double bonds with either cis or trans stereochemistry. Thus, one retinoid can have several stereoisomers depending upon the number of carbon-carbon double bonds. Although synthetic routes to retinoids have been developed, they do not produce retinoids in high yield and stereoselectivity. The methods described herein address this need.

SUMMARY

Described herein are methods for making retinoids. Also described herein are retinoids and methods of use thereof.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Figure 1:
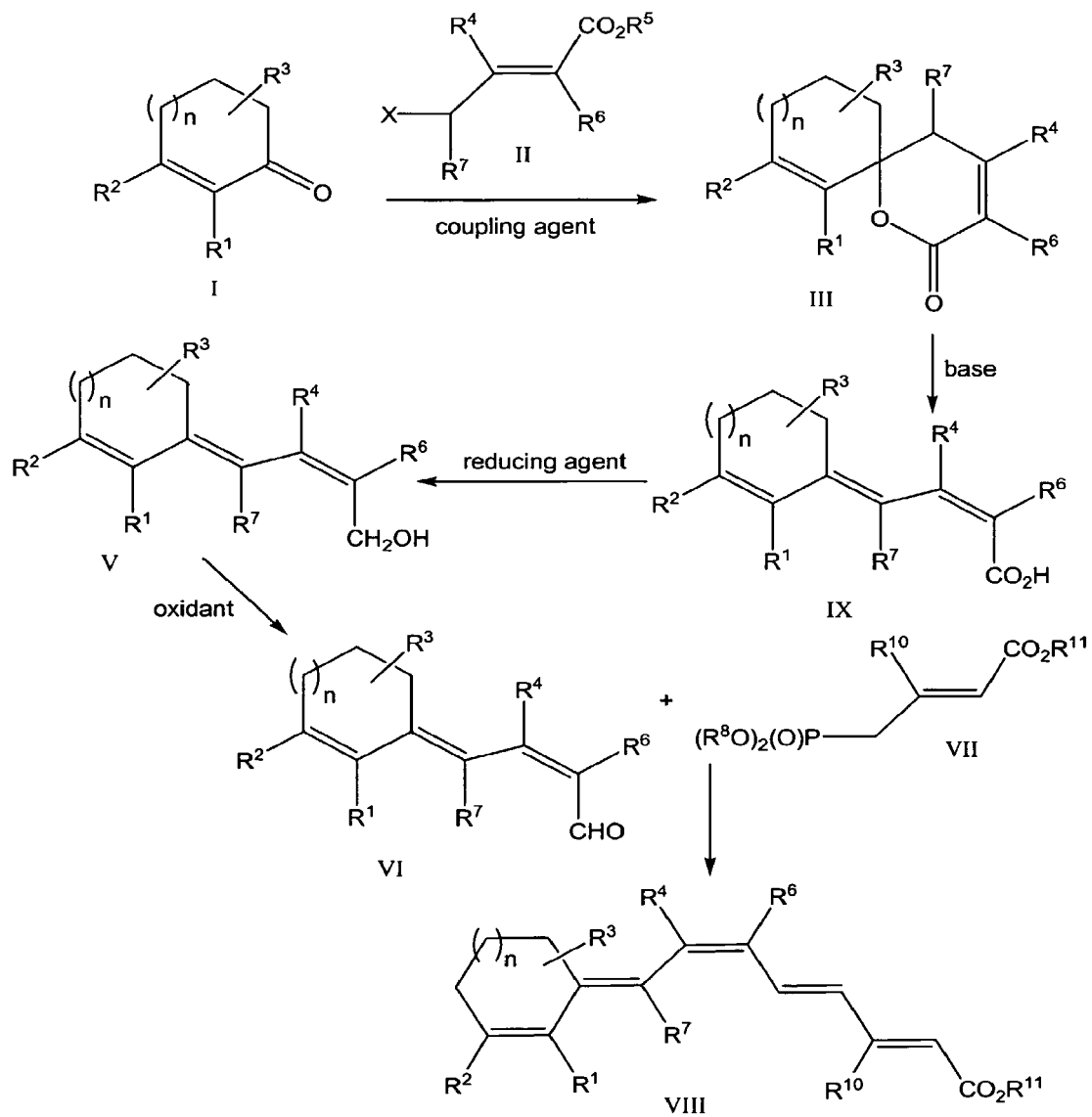
FIG. 1 shows a general reaction scheme for preparing retinoid compounds.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

The term "independently" when referring to two or more particular R groups present in a formula refers to any combination of variables listed for that particular R group. For example, in the formula —NRR', where R and R' are, independently, hydrogen, methyl, or ethyl, any combination of R and R' is contemplated. Thus, for example, when R is hydrogen, R' can be hydrogen, methyl, or ethyl.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^{11}$, X, and n used throughout the application are the same variables as previously defined unless stated to the contrary.

The term "substantially" with respect to E,Z-stereochemistry about a carbon-carbon double bond refers to greater than 95%, greater than 97%, greater than 98%, greater than 99%, greater than 99.5%, or 100% of one stereoisomer (E or Z) over the other. The term "substantially" with respect to enantiomeric purity refers to greater than 95%, greater than 97%, greater than 98%, greater than 99%, greater than 99.5%, or 100% of one enantiomer with respect to the other enantiomer.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

"Treatment" or "treating" means to administer a composition to a subject or a system with an undesired condition (e.g., cancer) or at risk for the condition. The condition can include a disease or a predisposition to a disease. The effect of the administration of the composition to the subject can have the effect of but is not limited to reducing or preventing the symptoms of the condition, a reduction in the severity of the condition, or the complete ablation of the condition.

By "effective amount" is meant a therapeutic amount needed to achieve the desired result or results, e.g., reducing or preventing the occurrence of a neoplastic condition.

The term "alkyl group" as used herein is a branched or unbranched saturated hydrocarbon group of 1 to 15 carbon atoms, such as methyl, ethyl, n-propyl, isopropyl, n-butyl, isobutyl, t-butyl, pentyl, hexyl, heptyl, octyl, decyl, or tetradecyl, and the like. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term cycloalkyl group also includes a heterocycloalkyl group, where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl group" also includes "heteroaryl group," which is defined as an aryl group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" as used herein is an aryl group having an alkyl group as defined above attached to the aryl group. An example of an aralkyl group is a benzyl group.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Additionally, if a generic formula has several variables, each and every combination of the variables in the formula is contemplated. For example, if an aryl ring is substituted with one or more $C_1$-$C_{15}$ alkyl groups, then every possible substitution about the aryl ring with respect to the different alkyl groups is contemplated.

I. Methods of Making Retinoid Compounds

Described herein are methods for producing retinoids. In one aspect, the reaction scheme depicted in FIG. 1 can be used to synthesize retinoid compounds. The stereochemistry about each of the double bonds in each of the compounds in FIG. 1 is exemplary. It is contemplated that the stereochemistry about each double bond can vary depending upon the selection of the starting materials, reagents, and reaction conditions. Referring to FIG. 1, in one aspect, the synthesis starts with reacting the cyclic ketone I with compound II in the presence of a coupling agent to produce the spirolactone compound III.

In one aspect, wherein $R^1$ and $R^2$ in formula I are, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group, or $R^1$ and $R^2$ collectively form a substituted or unsubstituted fused aryl group;

and $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group; and n is from 0 to 3, wherein one or more carbon atoms in the ring in formula I can optionally be replaced with a heteroatom. In the case of when $R^3$ is not hydrogen, the cyclic ketone can be racemic or substantially enantiomerically pure. It is also contemplated that the cyclic ketone has one or more $R^3$ groups. In the case when there are two or more $R^3$ groups, the groups can be the same or different. Additionally, when two different $R^3$ groups are present on the ring, they can be on the same carbon atom or on different carbon atoms of the ring. In other aspects, any of the carbon atoms in the cyclic ring of formula I can be replaced with a heteroatom (e.g., oxygen, sulfur, or nitrogen).

In one aspect, with respect to formula I, n is 1, and $R^1$ and $R^2$ are a $C_1$-$C_{15}$ branched or straight chain alkyl group or a substituted or unsubstituted cycloalkyl group. In another aspect, with respect to formula I, n is 1, $R^1$ is a $C_5$ or greater branched or straight chain alkyl group or a substituted or unsubstituted cycloalkyl group, and $R^2$ is a $C_1$-$C_{15}$ branched or straight chain alkyl group. In various aspects, with respect to formula I, n is 1; $R^1$ is an isopentyl group; $R^2$ is methyl, ethyl, propyl, isopropyl, butyl, isobutyl, phenyl, cyclopropyl, cyclobutyl, cyclopentyl, cyclohexyl, or benzyl; and $R^3$ is hydrogen.

In another aspect, the cyclic ketone I has the formula XI

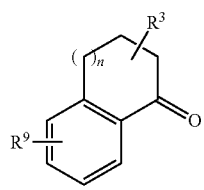

XI wherein $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group; and $R^9$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group, and n is from 0 to 3, wherein one or more carbon atoms in the cycloalkyl ring and/or aryl ring in formula XI can optionally be replaced with a heteroatom.

In one aspect, with respect to formula XI, n is 1 and (1) $R^3$ and $R^9$ are hydrogen; (2) $R^3$ is hydrogen and $R^9$ is one or more methyl groups; (3) $R^9$ is hydrogen and $R^3$ is one or more methyl groups; or (4) $R^3$ and $R^9$ is one or more methyl groups. In another aspect, the cyclic ketone having the formula XI is 4-methyl-1-tetralone, 5-methyl-1-tetralone, 6-methyl-1-tetralone, 7-methyl-1-tetralone, 8-methyl-1-tetralone, or 7-isopropyl-1-tetralone.

With respect to compound II (FIG. 1), $R^4$-$R^7$ are, independently, hydrogen, a $C_1$-$C_{15}$ branched or straight chain alkyl group, or a substituted or unsubstituted cycloalkyl group, and X is a halogen, wherein the stereochemistry about the carbon-carbon double bond in formula II is substantially E or Z. In one aspect, $R^4$ in formula II is a methyl group and X is bromide or chloride. In another aspect, $R^4$ in formula II is a methyl group, $R^5$ is an ethyl or methyl group, X is bromide or chloride, and $R^6$ and $R^7$ are hydrogen.

The reaction between I and II is performed in the presence of a coupling agent, which is any compound that can facilitate the reaction between the two compounds. In one aspect, the coupling agent comprises a zero-valent metal atom, a metal salt, or a mixture thereof, wherein the coupling agent is not zinc metal alone. In one aspect, the coupling agent comprises a mixture of (1) a zinc compound and (2) a rhodium compound or iron compound. In another aspect, the coupling agent comprises a mixture of a zinc compound and a copper compound. In a further aspect, the coupling agent comprises a mixture of zinc metal and a copper salt. Examples of copper salts include, but are not limited to, copper chloride, copper acetate, and the like.

The reaction between compounds I and II in the presence of the coupling agent is generally performed in the presence of a solvent. In one aspect, lower boiling solvents such as, for example THF, can be used. By using lower boiling solvents, decomposition of compound III can be reduced relative to the reaction performed at elevated temperatures. Compounds I, II, and the coupling agent can be added in any order. Reaction times and temperatures will vary depending upon the selection of compounds I, II, and the coupling agent. Compound III can be purified and characterized using techniques known in the art.

Referring to FIG. 1, eliminative ring-opening of compound III by reacting a compound III with a base produces compound IX, where $R^1$-$R^4$, $R^6$, $R^7$, and n are the same as defined above. U.S. Pat. No. 6,172,112, which is incorporated by reference in its entirety, discloses methods for the eliminative ring-opening of spirolactones that can be used herein. Examples of bases include, but are not limited to, NaOH, KOH, Ca(OH)$_2$, K$_2$CO$_3$, or Na$_2$CO$_3$. The conversion from compound III to compound IX can produce the E-isomer, the Z-isomer, or a mixture thereof. In one aspect, it is possible to go straight from compound I to compound IX without isolating compound III. In this aspect, compound III is produced in situ. In another aspect, it is contemplated to go straight from compound I to compound IX without producing compound III. For example, olefination reactions such as the Wittig, Horner-Wadsworth-Emmons, or Peterson olefinations are contemplated to convert compound I directly to compound IX, or to the ester derivative of IX.

Referring to FIG. 1, compound IX is converted to the primary alcohol V, where $R^1$-$R^4$, $R^6$, $R^7$, and n are the same as defined above, by reacting compound IX with a reducing agent in an alkyl ether. Numerous reducing agents are known in the art and can be selected depending upon the selection of compound IX. Examples of reducing agents include, but are not limited to, $LiAlH_4$, DIBAH, or diborane. In one aspect, the alkyl ether is a lower alkyl ether such as, for example, diethyl ether. By varying the solvent and the reaction temperature, it is possible vary the ratio of E- to Z-stereoisomers. In one aspect, compound IX is reacted with a reducing agent such as, for example, a preformed ether solution of $LiAlH_4$, to produce compound V that is substantially the Z-stereoisomer.

Referring to FIG. 1, compound V is oxidized to the aldehyde VI, where $R^1$-$R^4$, $R^4$, $R^7$, and n are the same as defined above.

In one aspect, with respect to formula V, n is 1, and $R^1$ and $R^2$ are a $C_1$-$C_{15}$ branched or straight chain alkyl group or a substituted or unsubstituted cycloalkyl group. In another aspect, with respect to formula V, n is 1, $R^1$ is a $C_5$ or greater branched or straight chain alkyl group or a substituted or unsubstituted cycloalkyl group, and $R^2$ is a $C_1$-$C_{15}$ branched or straight chain alkyl group. In various aspects, with respect to formula V, n is 1; $R^1$ is an isopentyl group; $R^2$ is methyl, ethyl, propyl, isopropyl, butyl, isobutyl, phenyl, cyclopropyl, cyclobutyl, cyclopentyl, cyclohexyl, or benzyl; and $R^3$ is hydrogen. In any of the preceding aspects, $R^6$ and $R^7$ can be hydrogen.

In one aspect, compound V has the formula XII

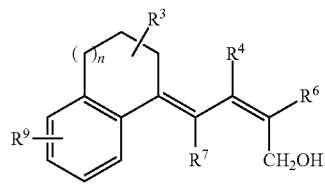

XII wherein $R^3$, $R^4$, $R^6$, $R^7$, $R^9$, and n are the same as defined above. In one aspect, with respect to formula XII, n is 1 and (1) $R^3$ and $R^9$ are hydrogen; (2) $R^3$ is hydrogen and $R^9$ is one or more methyl groups; (3) $R^9$ is hydrogen and $R^3$ is one or more methyl groups; or (4) $R^3$ and $R^9$ is one or more methyl groups. In any of the preceding aspects, $R^4$ can be methyl. In any of the preceding aspects, $R^6$ and $R^7$ can be hydrogen. In another aspect, compound V is (2Z,4E)-4-(3',4'-dihydro-4'-methyl-1'(2'H)-naphthalen-1'-ylidene))-3-methyl-2-buten-1-ol, (2Z,4E)-4-(3',4'-dihydro-5'-methyl-1'(2'H)-naphthalen-1'-ylidene))-3-methyl-2-buten-1-ol, (2Z,4E)-4-(3',4'-dihydro-6'-methyl-1'(2'H)-naphthalen-1'-ylidene))-3-methyl-2-buten-1-ol, (2Z,4E)-4-(3',4'-dihydro-7'-methyl-1'(2'H)-naphthalen-1'-ylidene))-3-methyl-2-buten-1-ol, (2Z,4E)-4-(3',4'-dihydro-8'-methyl-1'(2'H)-naphthalen-1'-ylidene))-3-methyl-2-buten-1-ol, or (2Z,4E)-4-(3',4'-dihydro-7'-isopropyl-1'(2'H)-naphthalen-1'-ylidene))-3-methyl-2-buten-1-ol.

The oxidant can be any compound capable of oxidizing a primary alcohol to the corresponding aldehyde. In one aspect, the oxidant comprises $H_2CrO_4$, $CrO_3$-pyridine, pyridinium chlorochromate, pyridinium dichromate, Fe(VI), a reagent for the Swern oxidation, dimethyl sulfide and N-chlorosuccinimide, tetramethyl piperidine nitroxide, acetic anhydride in DMSO, $P_2O_5$ in DMSO, tosyl chloride/triethyl amine, or Dess-Martin reagent. In another aspect, the oxidant is 2-iodoxybenzoic acid.

In a further aspect, the oxidant is not $MnO_2$. Large amounts of $MnO_2$ and powdered molecular sieves are required to produce the aldehyde VI. Consequently, the isolation and purification of the aldehyde is extremely tedious. Isolation of the aldehyde requires washing the $MnO_2$ with a substantial amount of solvent, at which time a considerable amount of aldehyde will decompose and result in very low yields. In contrast, the oxidants used herein require a simple filtration of the aldehyde product and concentration of the filtrate, which results in minimal decomposition and isomerization of the product.

Reaction times and temperatures will vary depending upon the selection of compound V and the oxidant. Compound VI can be purified and characterized using techniques known in the art.

Referring to FIG. 1, a compound having the formula VIII, where $R^1$-$R^4$, $R^6$, $R^7$, and n are defined above,

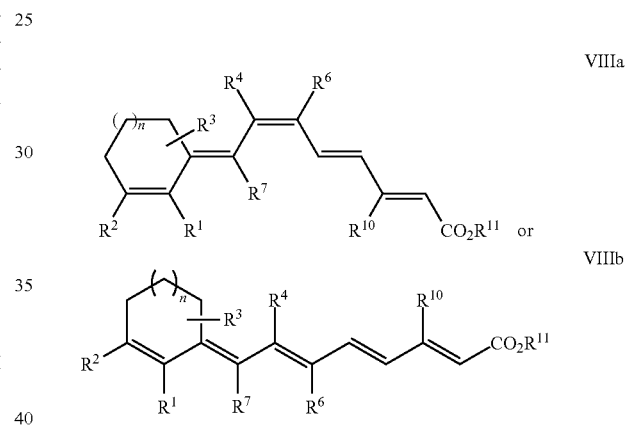

can be produced by reacting a compound having the formula VI with a compound having the formula VII

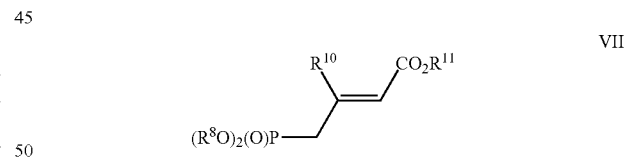

wherein $R^8$, $R^{10}$, and $R^{11}$ are, independently, hydrogen or a $C_1$-$C_{15}$ branched or straight chain alkyl group, wherein the stereochemistry about the carbon-carbon double bond in formula VII is substantially E or Z, or an E,Z-mixture.

in a solvent system comprising tetrahydrofuran and hexamethylphosphoramide, wherein the volumetric ratio of tetrahydrofuran to hexamethylphosphoramide is from 1:1 to 40:1.

In one aspect, with respect to formula VI, n is 1, and $R^1$ and $R^2$ are a $C_1$-$C_{15}$ branched or straight chain alkyl group. In another aspect, with respect to formula VI, n is 1, $R^1$ is a $C_5$ or greater branched or straight chain alkyl group, and $R^2$ is a $C_1$-$C_{15}$ branched or straight chain alkyl group. In another aspect, with respect to formula VI, n is 1; $R^1$ is an isopentyl group; $R^2$ is methyl, ethyl, propyl, isopropyl, butyl, isobutyl, phenyl, cyclopropyl, cyclobutyl, cyclopentyl, cyclohexyl, or benzyl; $R^3$ is hydrogen; and $R^4$ is methyl. In any of the preceding aspects, $R^6$ and $R^7$ are hydrogen, $R^{10}$ is methyl, and $R^{11}$ is hydrogen or a $C_1$-$C_{15}$ branched or straight chain alkyl group.

In another aspect, the compound having the formula VIa comprises the formula XV

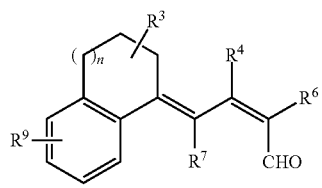

XV where $R^3$, $R^4$, $R^6$, $R^7$, $R^9$, and n are the same as defined above.

In one aspect, with respect to formula XV, n is 1 and (1) $R^3$ and $R^9$ are hydrogen; (2) $R^3$ is hydrogen and $R^9$ is one or more methyl groups; (3) $R^9$ is hydrogen and $R^3$ is one or more methyl groups; or (4) $R^3$ and $R^9$ is one or more methyl groups. In any of the preceding aspects, $R^4$ can be methyl. In any of the preceding aspects, $R^6$ and $R^7$ can be hydrogen. In any of the preceding aspects, $R^4$ and $R^{10}$ are methyl, $R^6$ and $R^7$ are hydrogen, and $R^{11}$ is hydrogen or a $C_1$-$C_{15}$ branched or straight chain alkyl group.

It is desirable to produce compound VIII as one stereoisomer or enriched with one stereoisomer. By varying the ratio of tetrahydrofuran and hexamethylphosphoramide, it is possible to produce compound VIII predominantly as one stereoisomer. Furthermore, purification of the compound is also facilitated when predominantly one stereoisomer of compound VIII is present. In one aspect, the volumetric ratio of tetrahydrofuran and hexamethylphosphoramide is 1:1 to 40:1; 1:1 to 30:1; 1:1 to 20:1; 1:1 to 10:1; 1:1 to 8:1; 1:1 to 6:1; or 1:1 to 4:1.

Prior to producing compounds having the formula VIII, the starting material VIa and VIb can be isomerized to the other stereoisomer (i.e., Z to E or E to Z about the $R^4C=CR^6$ bond) using techniques known in the art such as, for example, reacting compound VIa or VIb with iodine.

In the case when $R^{11}$ in compound VIII is not hydrogen, the ester can be converted to the corresponding acid using techniques known in the art. For example, treatment of the ester form of compound VIII with a base such as, for example, KOH, NaOH, $Ca(OH)_2$, $K_2CO_3$, or $Na_2CO_3$ can be used to convert the ester to the acid form.

In one aspect, purification of compound VIII comprises
(a) dissolving the compound in a solvent to produce a homogeneous solution;
(b) cooling the homogeneous solution to produce crystals of the compound and a second solution; and
(c) removing the second solution.

The method generally involves the recrystallization of compound VIII. Depending upon the nature and amount of stereoisomers present and the solvent selected, one stereoisomer of compound VIII can be crystallized from a mixture of two or more compounds. In general, organic solvents can be used to dissolve compound VIII. In one aspect, the organic solvent comprises one or more branched or straight chain aliphatic compounds such as, for example, those derived from pentane, hexane, heptane, octane, or nonane. The temperature and duration of the cooling step (b) will vary depending upon compound VIII and the solvent selected. In one aspect, the cooling step (b) is conducted at from 0° C. to −78° C. In another aspect, the cooling step (b) is from 10 minutes to 48 hours.

In one aspect, described herein is a method for making a compound having the formula XX

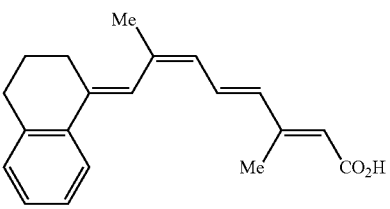 [SMILES: CC(=C/C=C/C(C)=C/C(=O)O)/C=C1\CCCc2cccc(C)c21]

XX comprising
(a) reacting a compound having the formula XXI

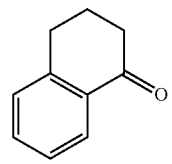

XXI with a compound having the formula XXII,

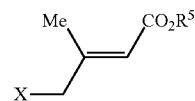

XXII wherein $R^5$ is hydrogen, a $C_1$-$C_{15}$ branched or straight chain alkyl group, or a substituted or unsubstituted cycloalkyl group, and X is a halogen, wherein the stereochemistry about the carbon-carbon double bond in formula XXII is substantially E or Z, or an E,Z-mixture, in the presence of a coupling agent, wherein the coupling agent comprises a zero-valent metal atom, a metal salt, or a mixture thereof, wherein the coupling agent is not zinc metal alone to produce a first compound having the formula XXIII

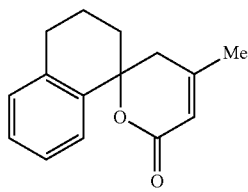

XXIII (b) reacting the first compound with a base to produce a second compound having the formula XXIV

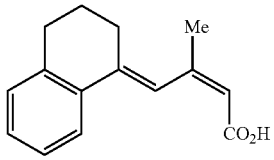

XXIV (c) reacting the second compound with a reducing agent to produce a third compound having the formula XXV

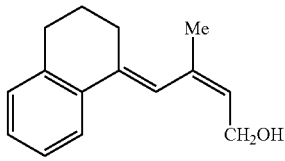

XXV (d) reacting the third compound with an oxidant, wherein the oxidant comprises a compound capable of oxidizing a primary alcohol to the corresponding aldehyde, wherein the oxidant is not $MnO_2$, to produce a fourth compound having the formula XXVI

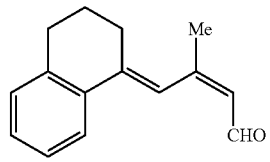

XXVI (e) reacting the fourth compound with a compound having the formula XXVII

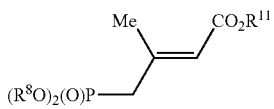

XXVII wherein $R^8$ and $R^{11}$ are, independently, a $C_1$-$C_{15}$ branched or straight chain alkyl group, wherein the stereochemistry about the carbon-carbon double bond in formula XXVII is substantially E or Z, or an E,Z-mixture, in a solvent system comprising tetrahydrofuran and hexamethylphosphoramide, wherein the volumetric ratio of tetrahydrofuran to hexamethylphosphoramide is from 1:1 to 40:1 to produce a fifth compound having the formula XXVIII

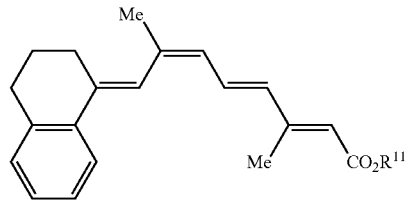

XXVIII (f) hydrolyzing the fifth compound to convert the ester to the compound having the formula XX or the pharmaceutically-acceptable salt thereof; and (g) purifying the compound having the formula XX comprising
  (i) dissolving the fifth compound in a solvent to produce a homogeneous solution;
  (ii) cooling the homogeneous solution to produce crystals of the compound and a second solution; and
  (iii) removing the second solution.

II. Compounds and Compositions a. Compounds

In one aspect, described herein are compounds having the formula XXX

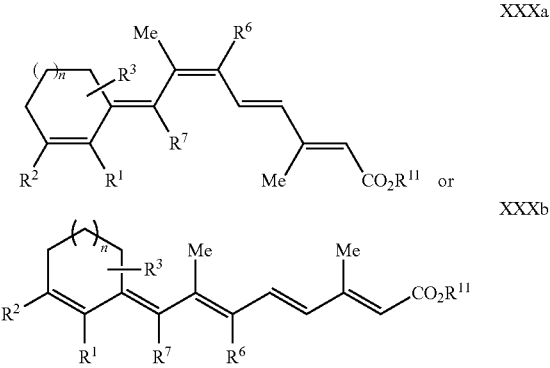

XXXa or

XXXb wherein $R^1$ is a $C_5$ or greater branched or straight chain alkyl group;

$R^2$ is hydrogen, a $C_1$-$C_{15}$ branched or straight chain alkyl group, a substituted or unsubstituted aryl group, a substituted or unsubstituted aralkyl group, or a substituted or unsubstituted cycloalkyl group, or $R^1$ and $R^2$ collectively form a substituted or unsubstituted fused aryl group; and $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^6$ and $R^7$ are, independently, hydrogen, a $C_1$-$C_{15}$ branched or straight chain alkyl group, or a substituted or unsubstituted cycloalkyl group;

$R^{11}$ is hydrogen or a $C_1$-$C_{15}$ branched or straight chain alkyl group; and n is from 0 to 3, wherein one or more carbon atoms in the ring in formula XXX can optionally be replaced with a heteroatom, or the pharmaceutically-acceptable salt or ester thereof, wherein the compound is not (2E,4E,6Z,8E)-8-(3',4'-dihydro-1'(2'H-naphthalen-1'-ylidene))-3,7-dimethyl-2,4,6-octatrienoic acid or an ester thereof; (2E,4E,6E,8E)-8-(3',4'-dihydro-1'(2'H-naphthalen-1'-ylidene))-3,7-dimethyl-2,4,6-octatrienoic acid or an ester thereof; (2E,4E,6Z,8E)-8-(3',4'-dihydro-4' methyl-1'(2'H-naphthalen-1'-ylidene))-3,7-dimethyl-2,4,6-octatrienoic acid or an ester thereof; and (2E, 4E,6Z, 8E)-8-(3',4'-dihydro-5',7'-dimethyl-1'(2'H-naphthalen-1'-ylidene))-3,7-dimethyl-2,4,6-octatrienoic acid or an ester thereof.

In one aspect, with respect to formula XXX, n is 1, and $R^2$ is a $C_1$-$C_{15}$ branched or straight chain alkyl group. In another aspect, n is 1, R¹ is pentyl, isopentyl, neopentyl, hexyl, heptyl, octyl, nonyl, or decyl. In a further aspect, n is 1; R¹ is pentyl, isopentyl, neopentyl, hexyl, heptyl, octyl, nonyl, or decyl; and R² comprises a $C_1$-$C_{15}$ branched or straight chain alkyl group. In various aspects, R¹ is an isopentyl group; R² is methyl, ethyl, propyl, isopropyl, butyl, isobutyl, phenyl, cyclopropyl, cyclobutyl, cyclopentyl, cyclohexyl, or benzyl; $R^6$, $R^7$, and $R^{11}$ are hydrogen.

In one aspect, the compound having the formula XXX comprises the formula XXXI

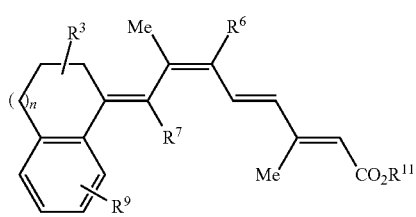

XXXI $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^6$ and $R^7$ are, independently, hydrogen, a $C_1$-$C_{15}$ branched or straight chain alkyl group, or a substituted or unsubstituted cycloalkyl group;

$R^9$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^{11}$ is hydrogen or a $C_1$-$C_{15}$ branched or straight chain alkyl group; and n is from 0 to 3, wherein the compound is not (2E,4E,6Z,8E)-8-(3',4'-dihydro-1'(2'H-naphthalen-1'-ylidene))-3,7-dimethyl-2,4,6-octatrienoic acid or an ester thereof; (2E,4E,6E,8E)-8-(3',4'-dihydro-1'(2'H-naphthalen-1'-ylidene))-3,7-dimethyl-2,4,6-octatrienoic acid or an ester thereof; (2E,4E,6Z,8E)-8-(3',4'-dihydro-4' methyl-1'(2'H-naphthalen-1'-ylidene))-3,7-dimethyl-2,4,6-octatrienoic acid or an ester thereof; and (2E,4E,6Z, 8E)-8-(3',4'-dihydro-5',7'-dimethyl-1'(2'H-naphthalen-1'-ylidene))-3,7-dimethyl-2,4,6-octatrienoic acid or an ester thereof.

In one aspect, with respect to compound XXXI, n is 1 and (1) $R^3$ is hydrogen and $R^9$ is one or more methyl groups, or (2) $R^9$ is hydrogen and $R^3$ is one or more methyl groups. In any of the preceding aspects, $R^6$, $R^7$, and $R^{11}$ can be hydrogen. In another aspect, compound XXXI is (2E,4E,6Z,8E)-8-(3',4'-dihydro-5'-methyl-1'(2'H-naphthalen-1'-ylidene))-3,7-dimethyl-2,4,6-octatrienoic acid (A); (2E,4E,6Z, 8E)-8-(3',4'-dihydro-6'-methyl-1'(2'H-naphthalen-1'-ylidene))-3,7-dimethyl-2,4,6-octatrienoic acid (B); (2E,4E,6Z,8E)-8-(3',4'-dihydro-7'-methyl-1'(2'H-naphthalen-1'-ylidene))-3,7-dimethyl-2,4,6-octatrienoic acid (C); (2E,4E,6Z,8E)-8-(3',4'-dihydro-7'-isopropyl-1'(2'H-naphthalen-1'-ylidene))-3,7-dimethyl-2,4,6-octatrienoic acid (D); or (2E,4E,6EZ 8E)-8-(3',4'-dihydro-8'-methyl-1'(2'H-naphthalen-1'-ylidene))-3,7-dimethyl-2,4,6-octatrienoic acid (E), which are depicted below in Table 1.

TABLE 1

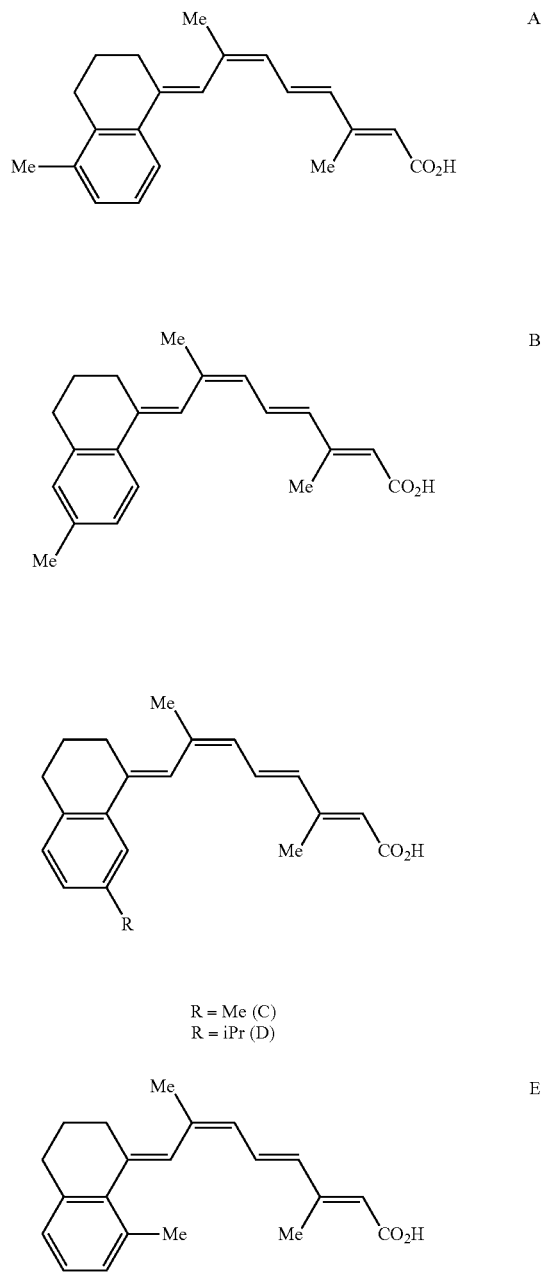

In another aspect, the non-fused retinoid compounds having the formula XXX are depicted below, where R is ethyl, isopropyl, cyclopropyl, or phenyl.

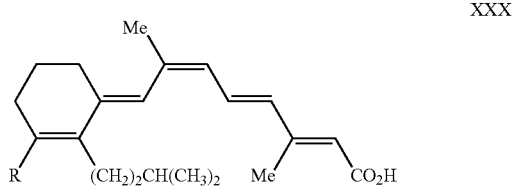

XXX

In another aspect, described herein are compounds having the formula XXXII

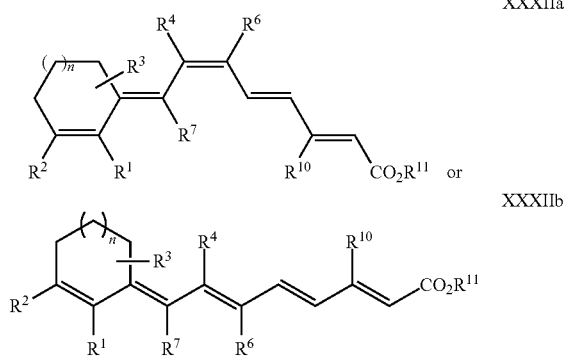

wherein $R^1$ and $R^2$ are, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group, or $R^1$ and $R^2$ collectively form a substituted or unsubstituted fused aryl group;

$R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^4$, $R^6$, and $R^7$ are, independently, hydrogen, a $C_1$-$C_{15}$ branched or straight chain alkyl group, or a substituted or unsubstituted cycloalkyl group;

$R^{10}$ and $R^{11}$ comprises, independently, hydrogen or a $C_1$-$C_{15}$ branched or straight chain alkyl group; and n is from 0 to 3, wherein one or more carbon atoms in the ring in formula XXXII can optionally be replaced with a heteroatom, or the pharmaceutically-acceptable salt or ester thereof, wherein $R^4$ and $R^{10}$ are not both a methyl group.

Any of the compounds synthesized by the methods described herein can exist or be converted to the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, di ethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

b. Pharmaceutical Compositions

Any of the compounds synthesized by the methods described herein can be formulated into a pharmaceutical composition. In one aspect, a compound having the formula VIII, XXX, or XXXII can be combined with at least one pharmaceutically-acceptable carrier to produce a pharmaceutical composition. The pharmaceutical compositions can be prepared using techniques known in the art. In one aspect, the composition is prepared by admixing the compound with a pharmaceutically-acceptable carrier. The term "admixing" is defined as mixing the two components together. Depending upon the components to be admixed the components may or may not chemically or physically interact with one another.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally, applied to the skin, etc.).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

It will be appreciated that the actual preferred amounts of active compound in a specified case will vary according to the specific compound being utilized, the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

III. Methods of Use

In one aspect, described herein are methods of treating a subject having a neoplastic condition or suspected of having a neoplastic or neoplastic-like condition by administering to the subject an effective amount of the compounds or compositions produced and disclosed herein. The compounds and compositions produced and disclosed herein can also reduce or prevent the occurrence of a neoplastic condition in a subject. In one aspect, the compound administered to the subject has the formula XXX or XXXII. In another aspect, the compound is further combined with 4-hydroxyphenylretinamide in the treatment. In other aspects, two or more compounds produced or disclosed herein can be administered to the subject. In one aspect, the neoplastic condition comprises breast cancer, lung cancer, colon cancer, or leukemia.

In another aspect, described herein is method for treating a subject having basal or squamous cell carcinoma comprising administering to the subject an effective amount of a compound having the formula VIII or a composition thereof

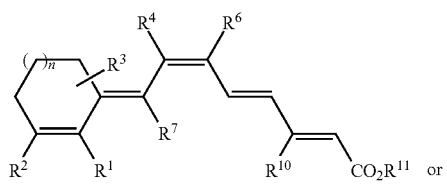

VIIIa

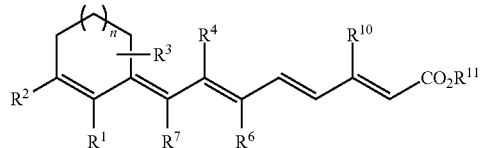

VIIIb wherein $R^1$ and $R^2$ are, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group, or $R^1$ and $R^2$ collectively form a substituted or unsubstituted fused aryl group; and $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^4$, $R^6$, and $R^7$ are, independently, hydrogen, a $C_1$-$C_{15}$ branched or straight chain alkyl group, or a substituted or unsubstituted cycloalkyl group;

wherein $R^{10}$ and $R^{11}$ are, independently, hydrogen or a $C_1$-$C_{15}$ branched or straight chain alkyl group, and n is from 0 to 3, wherein one or more carbon atoms in the ring in formula VIII can optionally be replaced with a heteroatom.

In one aspect, the compound has the formula XXXV

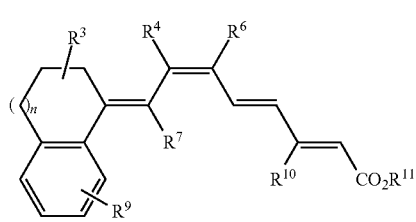

XXXV wherein $R^3$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^4$, $R^6$, and $R^7$ are, independently, hydrogen, a $C_1$-$C_{15}$ branched or straight chain alkyl group, or a substituted or unsubstituted cycloalkyl group;

$R^9$ is one or more groups comprising, independently, hydrogen, a $C_1$-$C_{15}$ branched or straight chain alkyl group, a substituted or unsubstituted aryl group, a substituted or unsubstituted aralkyl group, or a substituted or unsubstituted cycloalkyl group;

$R^{10}$ and $R^{11}$ are, independently, hydrogen or a $C_1$-$C_{15}$ branched or straight chain alkyl group, and n is from 0 to 3, wherein one or more carbon atoms in the ring in formula XXXV can optionally be replaced with a heteroatom.

In one aspect, in formula XXXV, n is 1 and $R^4$ and $R^{10}$ are methyl. In another aspect, the compound is

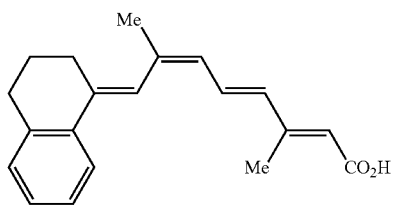

XX

In one aspect, described herein are methods for reducing serum triglycerides in a subject by administering to the subject an effective amount of the compounds or compositions produced and disclosed herein. The compounds described herein can be used as hypolipidemic drugs. In one aspect, the compounds herein can reduce serum triglycerides in a subject by 10%, 20%, 30%, 40%, 50%, 60%, 70%, 80%, or 90%. In one aspect, the compounds having the formula VIII can be used in these methods. In another aspect, the compound is (2E,4E,6E,8E)-8-(3',4'-dihydro-8'-methyl-1'(2'H-naphthalen-1'-ylidene))-3,7-dimethyl-2,4,6-octatrienoic acid and (2E,4E,6Z)-8-(3'-cyclopropyl-2'-(3-methylbutyl)-2'-cyclohexen-1'-ylidene))-3,7-dimethyl-2,4,6-octatrienoic acid.

The amount of compound administered to the subject will vary depending upon the subject, the malady to be treated, and the compound selected. In one aspect, the dosage range is from about 1 mg/kg to about 300 mg/kg, 10 mg/kg to about 300 mg/kg, 1 mg/kg to about 250 mg/kg, 1 mg/kg to about 200 mg/kg, 1 mg/kg to about 150 mg/kg, or 1 mg/kg to about 100 mg/kg of body weight.

Any of the compounds and compositions produced and described herein can be administered to a subject using a variety of administration or delivery techniques known in the art. In various aspects, the mode of administration can be oral or parenteral. The term "oral" is used herein to encompass administration of the compounds via the digestive tract. The term "parenteral" is used herein to encompass any route of administration, other than oral administration, by which the compound is introduced into the systemic circulation which includes, but is not limited to, intravenous, intramuscular, subcutaneous, intraperitoneal, intradermal, ocular, inhalable, rectal, vaginal, transdermal, topical, buccal, sublingual, or mucosal administration. The term "mucosal" as used herein encompasses the administration of the compounds by methods that employ the mucosa (mucous membranes) of the human body such as, but not limited to, buccal, intranasal, gingival, vaginal, sublingual, pulmonary, or rectal tissue. The term "transdermal" as used herein encompasses the administration of the compounds that go into the skin or go through the skin using formulations such as, but not limited to, transdermal formulations, buccal patches, skin patches, or transdermal patches. The term "topical" as used herein encompasses administration by applying conventional topical preparations such as creams, gels, or solutions for localized percutaneous delivery and/or by solution for systemic and/or localized delivery to areas such as, but not limited to the eye, skin, rectum, and vagina.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Melting points were obtained on an electrothermal melting point apparatus and are uncorrected. $^1$H and $^{13}$C NMR spectra were recorded on a Bruker ARX 300 spectrometer. Mass spectra were recorded on a MicroMass platform LCZ spectrometer. Atlantic Microlabs of Atlanta, Ga. provided combustion analyses. Solvents and liquid starting materials were distilled prior to use. Reactions and purifications were conducted with deoxygenated solvents, under inert gas ($N_2$), and in subdued lighting. Flash chromatography was performed using Selecto Scientific silica gel (40 µm). Ethyl 4-bromo-3-methylbut-2-enoate was prepared by the reaction of ethyl 3,3-dimethylacrylate with N-bromosuccinimide. Triethylphosphonosenecioate was prepared via the Arbusov reaction. Tetrahydrofuran was distilled from sodium metal/benzophenone ketyl. Diethyl ether, benzene, and dichloromethane were purchased from Fischer as anhydrous solvents. HMPA was distilled from calcium hydride.

Figure 2:
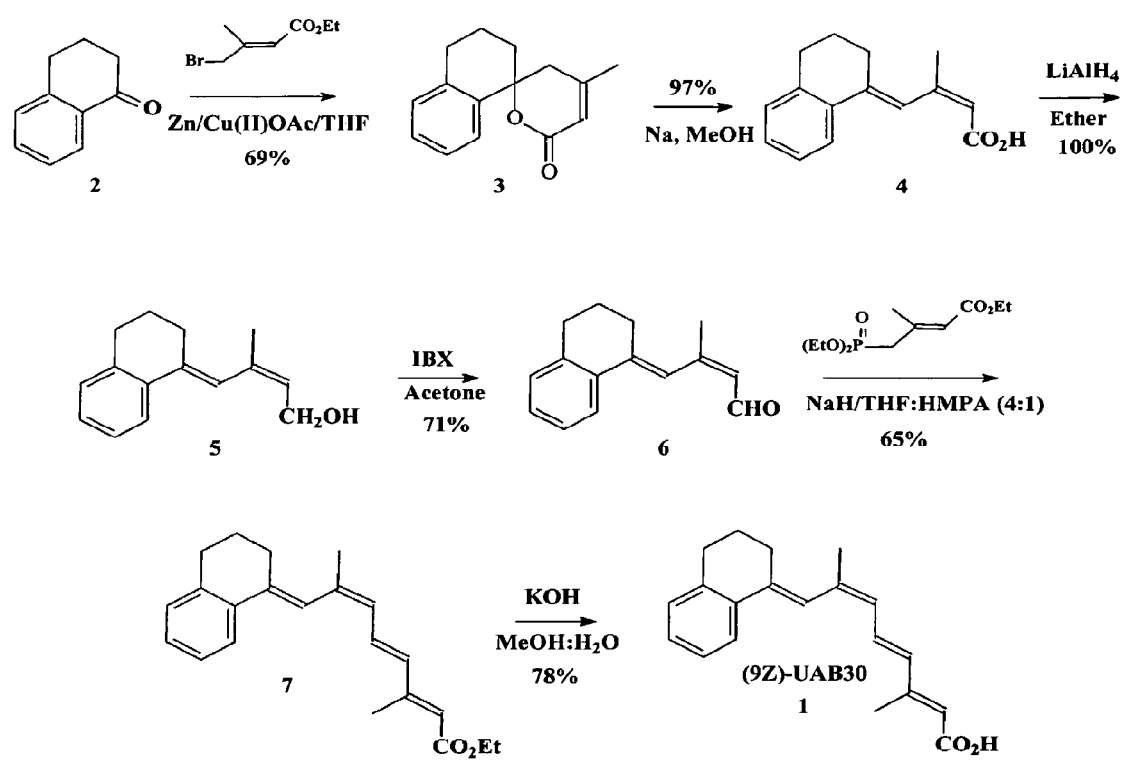
FIG. 2 shows a reaction scheme for preparing fused retinoid compounds.

I. Preparation of Fused Ring Retinoid Compounds (FIG. 2)

7,8-Benzo-4-methyl-1-oxaspiro[5.5]undec-3-en-2-one (3)

A mixture of zinc dust (150 g) (<10 micron, Aldrich, cat. no. 20, 998-8) and copper (II) acetate monohydrate (15 g, Acros) in 500 mL of glacial acetic acid was stirred rapidly under nitrogen for 1 hour in a 1000 mL, one-neck, roundbottomed flask. The mixture was diluted with anhydrous ether (500 mL), filtered with suction, and the Zn—Cu complex was washed successively with anhydrous ether (3×300 mL) and dry benzene (3×300 mL). The mixture was then transferred into a flame dried 2000 mL, three-neck flask fitted with a nitrogen inlet, condenser, and addition funnel. Freshly distilled THF (distilled from Na/benzophenone) (200 mL) was added to the flask, which was heated to about 90° C. in an oil bath with rapid stirring. The reaction mixture was then treated dropwise with a solution of tetralone 2 (100.0 g, 684.9 mmol, freshly distilled) and bromoester (220.0 g, 1063 mmol, freshly distilled) in 400 mL of THF (dry). Vigorous bubbling occurred during the addition. The mixture was stirred at reflux for an additional 3.5 hours. The reaction mixture was cooled to room temperature, and water (200 mL) and HCl (2 N, 500 mL) were added. The mixture was diluted with 1000 mL of ether, filtered, and the acid layer was separated. The organic layer was washed with water (2×200 mL), NaOH (1 N, 2×250 mL), and brine (2×250 mL). It was then dried ($Na_2SO_4$) and evaporated to give an oil. This oil was subjected to distillation on a high vacuum pump (0.1 mm) at 60° C. The distillate was discarded, and the remaining thick oily residue solidified upon addition of hexanes. This mixture was cooled, filtered, and washed with hexanes to give 108 g (69.2%) of 3 (Rf 0.3, 50:50 ether/hexane) as a white solid. mp 67-69° C. MS m/z 229 (M+1); $^1$H NMR (CDCl$_3$) δ7.5-7.54 (m, 1H), 7.2-7.25 (m, 2H), 7.07-7.1 (m, 1H), 5.92 (s, 1H), 2.7-2.9 (m, 3H), 2.5 (d, 1H), 1.98-2.23 (m, 3H), 2.01 (s, 3H), 1.67-1.78 (m, 1H).

(2Z,4E)-4-(3',4'-Dihydro-1'(2'H)-naphthalen-1'-ylidene))-3-methyl-2-butenoic Acid (4)

A solution of lactone 3 (70 g, 307 mmol) in anhydrous methanol (500 mL) was treated with small pieces of sodium metal (8.5 g, 369.5 mmol). The resulting mixture was stirred at reflux for 1 hour. Methanol was removed under vacuum and the resulting oil was dissolved in 1000 mL of water, cooled in an ice bath, and slowly acidified with 2N HCl to about pH 2. The resulting white precipitate was filtered, washed with ice-cold water, and air dried to give 68 g (97%) of pure acid 4: mp 153-154° C. (ethyl acetate/hexane); IR 1677 (C=O), 1618 (C=C) cm$^{-1}$; MS m/z 229 (M+1); NMR (CDCl$_3$) δ 7.6-7.7 (m, 1H), 7.15-7.25 (m, 3H), 7.07-7.1 (m, 1H), 5.8 (m, 1H), 2.8-2.75 (t, 2H), 2.6-2.55 (m, 2H), 2.1 (s, 3H), 1.9-1.8 (m, 2H).

(2Z,4E)-4-(3',4'-Dihydro-1'(2'H)-naphthalen-1'-ylidene))-3-methyl-2-buten-1-ol (5)

A solution of acid 4 (60.0 g, 263 mmol) in anhydrous ether (1000 mL) was cooled to 0° C. in an ice bath. This mixture was treated drop wise with a 1M solution of lithium aluminum hydride in ether (368 mL, 368 mmol) over a period of 1 hour. The resulting reaction mixture was stirred for an additional 1 hour at 0° C. The reaction mixture was cooled to −78° C. (dry ice/acetone bath) and quenched slowly with methanol (100 mL) followed by 10% $H_2SO_4$ (250 mL). The organic layer was separated and the aqueous layer was extracted with ether (4×250 mL). The combined organic layers were washed with brine (2×250 ml), dried (sodium sulfate) and concentrated on roto-evaporator below 30° C. to give 5 as a semi-solid, which solidified completely on a high vacuum pump. The crude yield was about 56-58 g (100%), product was pure by NMR and TLC, and these were used in the next reaction without further purification: mp 50-51° C. (ether/hexanes); IR 3334 (OH), 1612 (C=C) $cm^{-1}$; MS m/z 215 (M+1); $^1$H NMR ($CDCl_3$) δ 7.6-7.55 (m, 1H), 7.2-7.1 (m, 3H), 7.1-7.05 (m, 1H), 6.3 (s, 1H) 5.6-5.5 (m, 1H), 4.06 (d, 2H) 2.83 (t, 2H), 2.4-2.3 (m, 2H), 1.86 (s, 3H), 1.85-1.8 (m, 2H).

(2Z,4E)-4-(3',4'-Dihydro-1'(2'H)-naphthalen-1'-ylidene))-3-methyl-2-butenal (6)

A solution of alcohol 5 (56.0 g, 262 mmol) in acetone (2,400 mL) was treated with 2-iodoxybenzoic acid (IBX) (240 g, 857 mmol) in one addition. The resulting mixture was heated rapidly to 55-58° C. with stirring under subdued light. The mixture was stirred at that temperature for an additional 1 hour. The mixture was cooled in an ice bath for about 1 hour, filtered, washed with ether (1,000 mL) and concentrated (rotary evaporator, water bath temp. <35° C.). The resulting oil was purified by column chromatography (silica gel, 40×7 cm, 1:6 ether/hexanes, all column solvents purged with nitrogen) to give 39 g of (9Z)-6 (Rf 0.3) (71%). The (9Z)-6 was crystallized from hexanes/ether: mp 65-66° C. IR 1662 (C=O), 1609 (C=C) $cm^{-1}$; UV $λ_{max}$ 295 (ε 6000); MS m/z 213 (M+H); $^1$H NMR ($CDCl_3$) δ 9.64 (d, 1H), 7.64 (m, 1H), 7.13-7.25 (m, 3H), 6.57 (s, 1H), 6.0 (d, 1H), 2.86 (t, 2H), 2.50 (t, 2H), 2.09 (s, 3H), 1.82-1.90 (m, 2H).

(2E,4E,6Z,8E)-Ethyl 8-(3',4'-Dihydro-1'(2'H)-naphthalen-1'-ylidene))-3,7-dimethyl-2,4,6-octatrienoate (7)

Sodium hydride (60% suspension in mineral oil, 2.95 g, 73.8 mmol) was placed in a flame-dried, 3-neck, roundbottomed flask fitted with a nitrogen inlet, addition funnel, and rubber septum. Freshly distilled THF (from Na/benzophenone, 400 mL) was added, followed by freshly distilled phosphonate ester (19.45 g, 73.67 mmol). The resulting brown mixture was stirred for 15 minutes, and freshly distilled HMPA (50 mL) was introduced through a syringe. The flask was covered with aluminum foil and stirring was continued for 15 minutes. The aldehyde 6 (14.20 g, 66.98 mmol) in 100 mL of dry THF was added dropwise from the addition funnel (covered with aluminum foil). The reaction mixture was stirred for an additional 2.5 hours and was quenched with 50 mL of water and then diluted with 500 mL of ether. The aqueous layer was separated and washed with 100 mL of ether. The combined organic layers were washed with brine (2×150 mL), dried ($Na_2SO_4$), and evaporated to give a crude oil (35 g), which was suspended in methanol (75 mL, degassed with nitrogen). Ether was added until the mixture was homogeneous (about 20 mL), and the solution was cooled overnight at 0° C. to give a crystalline solid. This solid was filtered, washed with methanol, and dried to give 14 g (65%) of pure product (9Z)-7 as one isomer: mp 64-65° C. IR 1706 (C=O), 1602 (C=C) $cm^{-1}$; UV $λ_{max}$ 328 nm (ε 29,300); MS m/z 323 (M+H); $^1$H NMR ($CDCl_3$) δ. 7.62-7.68 (m, 1H), 7.11-7.22 (m, 3H), 6.65 (dd, 1H), 6.5 (s, 1H), 6.23 (d, 1H), 6.1 (d, 1H), 5.75 (s, 1H), 4.15 (q, 2H), 2.85 (t, 2H), 2.40 (dt, 2H), 2.22 (s, 3H), 1.97 (s, 3H), 1.78-1.87 (m, 2H), 1.27 (t, 3H).

(2E,4E,6Z,8E)-8-(3',4'-Dihydro-1'(2'H)-naphthalen-1'-ylidene))-3,7-dimethyl-2,4,6-octatrienoic Acid (UAB 30, 1)

Ester 7 (12.00 g, 37.26 mmol) was suspended in methanol (640 mL, degassed with nitrogen) and warmed to about 60° C. This mixture was treated with KOH solution (20.90 g, 372.7 mmol, in 220 mL of distilled and degassed water). The resulting mixture was stirred at reflux for 1 hour, cooled to 0° C. in an ice bath and diluted with 300 mL of ice cold water. The mixture was slowly acidified with ice cold 2 N HCl to about pH 2. The resulting precipitate was filtered, and the solid was redissolved in 500 mL of ether. The organic solution was washed with brine (3×150 mL), dried ($Na_2SO_4$), and concentrated on a rotary evaporator to about 75 mL of volume. The residual solution was diluted with 100 mL of degassed hexanes and cooled at 0° C. for about 12 hours. The resulting yellow crystals were filtered and dried to give 8.5 g (78%) of pure (9Z)-1 (9Z-UAB 30): mp 175-176° C. IR 1672 (C=O), 1594 (C=C) $cm^{-1}$; UV $λ_{max}$ 328 nm (ε 30,200); MS m/z 295 (M+H); $^1$H NMR ($CDCl_3$) δ 11.00 (br, 1H), 7.6-7.67 (m, 1H), 7.15-7.21 (m, 2H), 7.11-7.14 (m, 1H), 6.68 (dd, 1H), 6.47 (s, 1H), 6.25 (d, 1H), 6.12 (d, 1H), 5.77 (s, 1H), 2.85 (t, 2H), 2.40 (dt, 2H), 2.22 (s, 3H), 1.98 (s, 3H), 1.79-1.87 (m, 2H).

Figure 3:
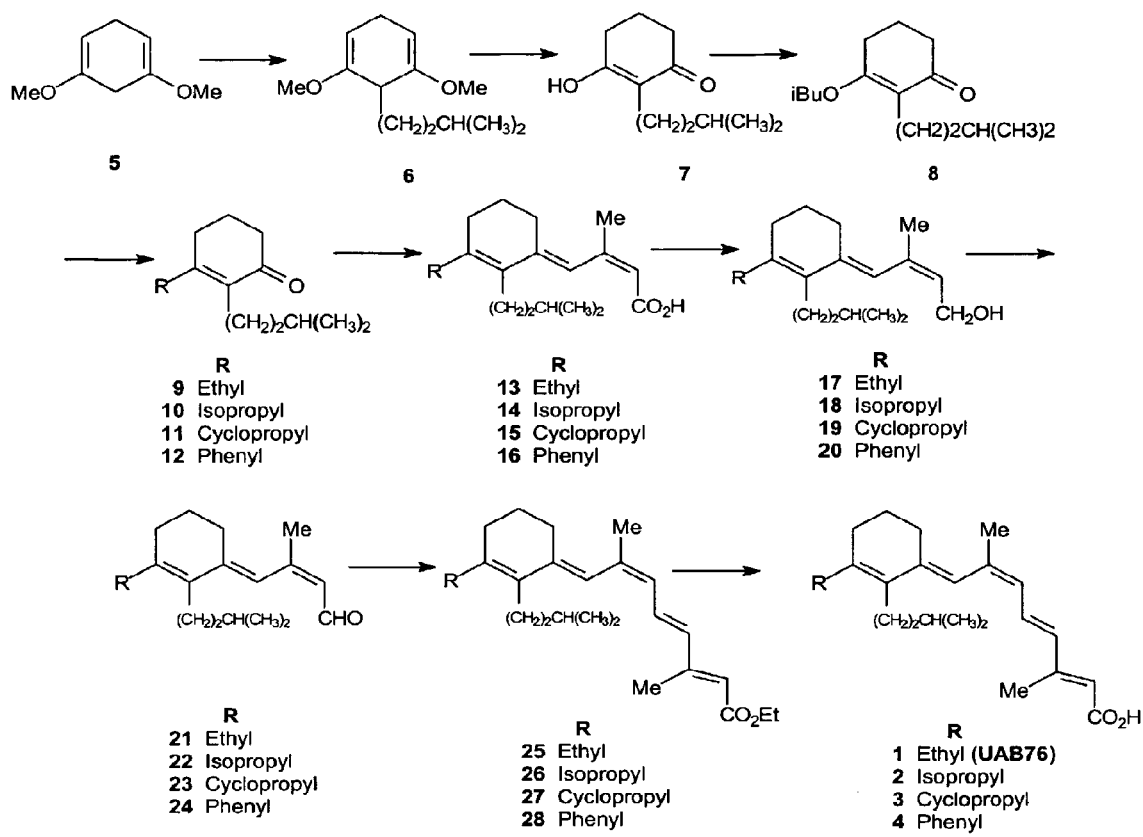
FIG. 3 shows a reaction scheme for preparing non-fused retinoid compounds.

II. Preparation of Non-Fused Ring Retinoid Compounds (FIG. 3)

2,4-Dimethoxy-3-(3-methylbutyl)-1,4-cyclohexadiene (6)

A solution of diene 5 (60.1 g, 429 mmol) in anhydrous THF (650 mL) was cooled to −78° C. This solution was slowly treated with tert-BuLi (1.7 M in pentane, 278 mL, 472 mmol). The resulting golden yellow solution was allowed to stir for 15 minutes, during which a fine precipitate developed. To this was slowly added freshly distilled 1-bromo-3-methylbutane (110 g, 728 mmol), and the mixture was stirred at −78° C. for 15 min. The cold bath was removed and the mixture was allowed to stir for 2 hours. To this was added slowly 250 mL of water. The mixture was diluted with diethyl ether (200 mL) and the organic layer was separated. The aqueous layer was extracted with ether (200 mL) and the combined organic layers were washed with brine (250 mL), dried (sodium sulfate) and concentrated to give 84 g (93%) of pure 6 as an oil, which was used in the next step without any further purification. MS m/z 211 (M+1); $^1$H NMR (300 MHz, $CDCl_3$) δ 4.7 (t, 2H), 3.5 (s, 6H), 2.9-2.8 (m, 1H), 2.8-2.7 (m, 2H), 1.7-1.6 (m, 2H), 1.5-1.4 (m, 1H), 1.0-0.9 (m, 2H), 0.8 (d, 6H); $^{13}$C NMR ($CDCl_3$) δ 155.0, 91.8, 54.6, 41.2, 33.6, 28.5, 27.8, 24.9, 23.1.

2-(3-Methylbutyl)-1,3-cyclohexanedione (7)

A suspension of ether 6 (84.0 g, 400 mmol) and 1N HCl (25 mL) was heated to 90° C. while stirring vigorously. After about 15 minutes the mixture became exothermic and a clear homogeneous liquid resulted. The reaction mixture was stirred for an additional 15 minutes at this temperature and cooled to room temp. During this process the product solidified, and the mixture was diluted with water (500 mL) and filtered. The solid was suspended in hexanes (250 mL), stirred, filtered and dried to give 68.0 g (93.4%) of 7. MS m/z 183 (M+1); $^1$H NMR (300 MHz, $CDCl_3$) δ 9.5-9.0 (br s, 1H), 2.5 (t, 4H), 2.3-2.2 (m, 2H), 2.0-1.9 (m, 2H), 1.6-1.5 (m, 1H), 1.2-1.1 (m, 2H), 0.9 (d, 6H); $^{13}$C NMR (CDCl$_3$) δ 206.0, 188.1, 117.2, 40.1, 38.1, 33.3, 28.6, 23.0, 21.2, 20.2

2-(3-Methylbutyl)-3-(2-methylpropyloxy)-2-cyclohexenone (8)

A solution of ketoenol 7 (68.0 g, 374 mmol), isobutanol (83.0 g, 1120 mmol), and p-toluenesulfonic acid (1.0 g, 1.2 mmol) in anhydrous benzene (730 mL) was refluxed overnight with azeotropic removal of water (Dean-Stark trap). The reaction mixture was cooled to room temperature, washed with saturated sodium bicarbonate solution (3×250 mL), brine (2×250 mL) and concentrated to give 88.0 g (98.9%) of 8 as a thick oil, which solidified upon cooling. MS m/z 239 (M+1); $^1$H NMR (300 MHz, CDCl$_3$) δ 3.75 (d, 2H), 2.5 (t, 2H), 2.3-2.2 (m, 4H), 2.0-1.9 (m, 3H), 1.6-1.5 (m, 1H), 1.2-1.1 (m, 2H), 1.0 (d, 6H), 0.9 (d, 6H); $^{13}$C NMR (CDCl$_3$) δ 198.4, 171.5, 120.1, 73.9, 38.0, 36.5, 28.8, 28.4, 25.5, 22.6, 21.1, 20.1, 19.1.

Procedure for making alkyl lithiums: using the following general procedure, cyclopropyl lithium and ethyl lithium were prepared.

Cyclopropyl Lithium. A three neck round bottomed flask containing anhydrous ether (150 mL) was treated with lithium ribbon (10.0 g, 1440 mmol) cut into small pieces. The mixture was cooled to −10° C. (methanol/ice) and treated dropwise with freshly distilled cyclopropyl bromide (60.0 g, 496 mmol) in ether (200 mL). The reaction mixture was stirred for an additional 3 hours at 0-5° C. This mixture was directly used in the next reaction without any further purification.

Procedure for preparing substituted cyclohexenones 9-12 (FIG. 3): using the following general procedure, all of the intermediate ketones were prepared.

3-Ethyl-2-(3-methylbutyl)-2-cyclohexenone (9)

A solution of isobutyl ether 8 (88.0 g, 370 mmol) in anhydrous ether (250 mL) was cooled to 0° C. in an ice bath and treated dropwise with ethyl lithium (650 mL). The resulting mixture was stirred at 0° C. for 2 hours and then at room temperature for 48 hours. The reaction mixture was slowly quenched with water (200 mL) and extracted with ether (2×200 mL). The combined organic layer was dried (Na$_2$SO$_4$) and concentrated under vacuum to provide 75 g of crude oil, which was purified by chromatography (silica gel; hexane/ether 4:1) to give 58.0 g (80.1%) of 9 as an oil: MS m/z 195 (M+1); $^1$H NMR (300 MHz, CDCl$_3$) δ 2.4-2.3 (m, 4H), 2.3-2.2 (m, 4H), 1.95-1.85 (m, 2H), 1.6-1.5 (m, 1H), 1.2-1.1 (m, 2H), 1.1 (t, 3H), 0.9 (d, 6H); $^{13}$C NMR (CDCl$_3$) δ 199.2, 159.9, 135.4, 39.0, 38.1, 30.0, 28.5, 27.8, 22.9, 22.6, 22.5, 12.4.

3-Isopropyl-2-(3-methylbutyl)-2-cyclohexenone (10)

MS m/z 209 (M+1); $^1$H NMR (300 MHz, CDCl$_3$) δ 3.0-2.9 (m, 1H), 2.38 (t, 2H), 2.3-2.2 (m, 4H), 1.9-1.8 (m, 2H), 1.6-1.5 (m, 1H), 1.2-1.1 (m, 2H), 1.06 (d, 6H), 0.90 (d, 6H); $^{13}$C NMR (CDCl$_3$) δ 199.9, 163.8, 135.0, 39.5, 38.7, 31.4, 28.9, 24.9, 23.2, 23.1, 22.9, 20.7.

3-Cyclopropyl-2-(3-methylbutyl)-2-cyclohexenone (11)

MS m/z 207 (M+1); $^1$H NMR (300 MHz, CDCl$_3$) δ 2.5-2.4 (m, 2H), 2.4-2.3 (m, 2H), 1.95-1.80 (m, 5H), 1.6-1.5 (m, 1H), 1.3-1.2 (m, 2H), 0.9 (d, 6H), 0.9-0.8 (m, 2H), 0.8-0.7 (m, 2H); $^{13}$C NMR (CDCl$_3$) δ 198.3, 159.0, 136.6, 38.8, 38.3, 28.8, 24.6, 23.1, 22.9, 22.5, 14.8, 6.8.

2-(3-Methylbutyl)-3-phenyl-2-cyclohexenone (12)

MS m/z 243 (M+1); $^1$H NMR (300 MHz, CDCl$_3$) δ 7.4-7.3 (m, 3H), 7.17 (d, 2H), 2.6 (t, 2H), 2.5 (t, 2H), 2.2-2.0 (m, 4H), 1.4-1.3 (m, 1H), 1.2-1.1 (m, 2H), 0.7 (d, 6H); $^{13}$C NMR (CDCl$_3$) δ 199.9, 157.1, 141.9, 137.4, 128.7, 128.0, 127.0, 39.2, 38.6, 33.8, 28.6, 24.9, 23.2, 22.7

Reformatsky reaction for preparing intermediate acids 13-16 (FIG. 3): using the following general procedure, all of the intermediate acids were prepared.

(2Z)-4-(3'-Ethyl-2'-(3-methylbutyl)-2'-cyclohexen-1'-ylidene))-3-methyl-2-butenoic Acid (13)

In a three neck round bottomed flask, zinc dust (42 g) was stirred with 10% HCl (150 mL) for 10 hours under a nitrogen atmosphere. The aqueous layer was decanted and the zinc was washed successively with distilled water (3×150 mL), anhydrous acetone (3×150 mL) and anhydrous ether (3×150 mL). After removing the residual ether the zinc dust was heated strongly with a Bunsen burner flame for about a minute under vacuum. The clumps of zinc were then carefully broken up with a stirring rod. The cooled zinc was suspended in anhydrous dioxane (200 mL), and the stirred suspension was heated to 125° C. in an oil bath. A solution of ketone 9 (47.0 g, 242 mmol), ethyl bromosenecioate (120 g, 579 mmol) and anhydrous dioxane (200 mL) was added to the reaction mixture dropwise over a period of 1 hour. The addition produced an exothermic reaction. The final reaction mixture was stirred at this temperature for an additional 2.5 hours. The reaction mixture was cooled to room temperature and water (100 mL) was added. The mixture was stirred for 15 minutes, and ether (500 mL) and 2N HCl (250 mL) were added. The mixture was filtered and the organic layer was washed with water (2×100 mL) followed by 1N NaOH (3×150 mL). The basic wash was cooled in an ice bath, the pH was adjusted to 2-3 with 2N HCl, and the mixture was extracted with ether (2×200 mL). The organic layer was dried (Na$_2$SO$_4$) and concentrated under vacuum to provide a semisolid. This was crystallized from hexanes/ether, filtered and dried to give 41 g (61.5%) of pure 13: mp 71-73° C.; MS m/z 277 (M+1); $^1$H NMR (300 MHz, CDCl$_3$) δ 6.6 (s, 1H), 5.7 (s, 1H), 2.3-2.2 (m, 4H), 2.2-2.1 (m, 4H), 2.1 (s, 3H), 1.7-1.6 (m, 2H), 1.6-1.5 (m, 1H), 1.4-1.3 (m, 2H), 1.0 (t, 3H), 0.9 (d, 6H); $^{13}$C NMR (CDCl$_3$) δ 171.1, 157.2, 141.7, 141.2, 132.0, 120.2, 116.9, 38.7, 30.2, 28.8, 28.7, 27.7, 25.9, 25.8, 22.9, 22.5, 12.8.

(2Z)-4-(3'-Isopropyl-2'-(3-methylbutyl)-2'-cyclohexen-1'-ylidene))-3-methyl-2-butenoic Acid (14)

mp 100-102° C.; MS m/z 291 (M+1); $^1$H NMR (300 MHz, CDCl$_3$) δ 6.6 (s, 1H), 5.7 (s, 1H), 2.96-2.9 (m, 1H), 2.4-2.2 (m, 4H), 2.1 (s, 3H), 2.1-2.0 (m, 2H) 1.6-1.5 (m, 3H), 1.4-1.3 (m, 2H), 1.0 (d, 6H), 0.9 (d, 6H); $^{13}$C NMR (CDCl$_3$) δ 171.8, 157.7, 145.5, 141.8, 131.6, 120.9, 117.4, 39.2, 30.8, 29.3, 29.2, 26.2, 26.0, 24.7, 23.4, 22.9, 21.0.

(2Z)-4-(3'-Cyclopropyl-2'-(3-methylbutyl)-2'-cyclohexen-1'-ylidene))-3-methyl-2-butenoic Acid (15)

mp 82-84° C.; MS m/z 289 (M+1); $^1$H NMR (300 MHz, CDCl$_3$) δ 12.0-10.0 (br s, 1H), 6.6 (s, 1H), 5.7 (s, 1H), 3.0-2.9 (m, 1H), 2.3-2.2 (m, 4H), 2.1 (s, 3H), 2.1-1.9 (m, 2H), 1.7-1.5 (m, 3H), 1.3-1.2 (m, 2H), 1.0 (d, 6H), 0.9 (d, 6H); $^{13}$C NMR (CDCl$_3$) δ 171.9, 157.5, 141.6, 139.4, 134.4, 120.3, 117.3, 38.5, 29.1, 28.9, 26.5, 26.3, 25.9, 23.1, 22.9, 14.7, 5.3.

(2Z)-4-(2'-(3-Methylbutyl)-3'-phenyl-2'-cyclohexen-1'-ylidene))-3-methyl-2-butenoic Acid (16)

mp 136-138° C.; MS m/z 325 (M+1); $^1$H NMR (300 MHz, CDCl$_3$) δ 7.4-7.3 (m, 2H), 7.3-7.2 (m, 1H), 7.2-7.1 (m, 2H), 6.7 (s, 1H), 5.7 (s, 1H), 2.44 (t, 2H), 2.37 (t, 2H), 2.2-2.1 (m, 2H), 2.1 (s, 3H), 1.8-1.7 (m, 2H), 1.4-1.2 (m, 3H), 0.7 (d, 6H); $^{13}$C NMR (CDCl$_3$) δ 171.9, 157.2, 145.0, 141.1, 140.2, 135.0, 128.5, 128.1, 126.7, 122.7, 117.9, 39.2, 34.2, 28.8, 27.7, 26.9, 26.2, 23.5, 22.7.

General procedure for the reduction of intermediate acids 13-16 to provide alcohols 17-20 (FIG. 3): Using the following general procedure, all of the intermediate alcohols were prepared.

(2Z)-4-(3'-Ethyl-2'-(3-methylbutyl)-2'-cyclohexen-1'-ylidene))-3-methyl-2-butenol (17)

A solution of acid 13 (40.0 g, 145 mmol) in anhydrous ether (800 mL) was cooled to 0° C. in an ice bath, and 1 M LiAlH$_4$/ether (200 mL, 200 mmol) was added dropwise with stirring. The reaction mixture was stirred at 0° C. for an additional 1 hour. The reaction mixture was cooled to −78° C., and methanol (100 mL) followed by 10% H$_2$SO$_4$ (200 mL) was added dropwise. The mixture was warmed to room temperature, and the organic layer was separated. The aqueous layer was extracted with ether (3×200 mL). The combined ether layers were washed with brine (2×100 mL), dried (Na$_2$SO$_4$) and concentrated under vacuum to provide 38 g (100%) of 17 as a colorless oil, which was used in the next reaction without further purification. MS m/z 263 (M+1); $^1$H NMR (300 MHz, CDCl$_3$) δ 5.8 (s, 1H), 5.5-5.4 (m, 1H), 4.0 (d, 2H), 2.3-2.2 (m, 2H), 2.1-2.0 (m, 6H), 1.8 (s, 3H), 1.7-1.5 (m, 3H), 1.3-1.2 (m, 2H), 1.0 (t, 3H), 0.9 (d, 6H); $^{13}$C NMR (CDCl$_3$) δ 139.3, 138.1, 137.4, 131.1, 125.3, 119.7, 61.2, 38.9, 30.2, 28.8, 27.9, 27.3, 25.5, 24.2, 23.2, 22.6, 12.9.

(2Z)-4-(3'-Isopropyl-2'-(3-methylbutyl)-2'-cyclohexen-1'-ylidene))-3-methyl-2-butenol (18)

MS m/z 277 (M+1); $^1$H NMR (300 MHz, CDCl$_3$) δ 5.8 (s, 1H), 5.5-5.4 (m, 1H), 4.0 (d, 2H), 2.9-2.8 (m, 1H), 2.3-2.2 (m, 2H), 2.1-2.0 (m, 4H), 1.8 (s, 3H), 1.6-1.5 (m, 3H), 1.3-1.2 (m, 2H), 1.0 (d, 6H), 0.9 (d, 6H).

(2Z)-4-(3'-Cyclopropyl-2'-(3-methylbutyl)-2'-cyclohexen-1'-ylidene))-3-methyl-2-butenol (19)

MS m/z 275 (M+1); $^1$H NMR (300 MHz, CDCl$_3$) δ 5.8 (s, 1H), 5.5-5.4 (m, 1H), 4.0 (d, 2H), 2.5-2.4 (m, 2H), 2.1-2.0 (m, 2H), 1.8 (s, 3H), 1.8-1.7 (m, 3H), 1.6-1.5 (m, 3H), 1.4-1.3 (m, 2H), 0.9 (d, 6H), 0.7-0.6 (m, 2H), 0.6-0.5 (m, 2H).

(2Z)-4-(2'-(3-Methylbutyl)-3'-phenyl-2'-cyclohexen-1'-ylidene))-3-methyl-2-butenol (20)

MS m/z 311 (M+1); $^1$H NMR (300 MHz, CDCl$_3$) δ 7.4-7.3 (m, 2H), 7.3-7.2 (m, 1H), 7.2-7.1 (m, 2H), 5.9 (s, 1H), 5.6-5.5 (m, 1H), 4.0 (d, 2H), 2.4-2.3 (m, 2H), 2.3-2.2 (m, 2H), 2.2-2.1 (m, 2H), 1.8 (s, 3H), 1.8-1.7 (m, 3H), 1.3-1.2 (m, 2H), 0.7 (d, 6H).

General procedure for the oxidation of alcohols 17-20 to give aldehydes 21-24 (FIG. 3): Using the following general procedure, all of the intermediate aldehydes were prepared.

(2Z)-4-(3'-Ethyl-2'-(3-methylbutyl)-2'-cyclohexen-1'-ylidene))-3-methyl-2-butenal (21)

A solution of crude alcohol 17 (38.0 g, 145 mmol) in acetone (1600 mL) was treated with 2-iodoxybenzoic acid (IBX) (125 g, 446 mmol) in one addition. The resulting mixture was heated rapidly to 55-58° C. with stirring under subdued light. The mixture was stirred at that temperature for an additional 1 hour. The mixture was cooled in an ice bath for about 1 hour, filtered, washed with ether (1000 mL) and concentrated (rotary evaporator, water bath temp. <35° C.). The resulting oil was purified by column chromatography (silica gel, 1:6 ether/hexanes, all column solvents purged with nitrogen) to give 27.2 g (73.0%) of (9Z) 21 and 0.5 g of (all E) 21. MS m/z 261 (M+1); $^1$H NMR (300 MHz, CDCl$_3$) δ 9.5 (d, 1H), 6.0 (s, 1H), 5.95-5.9 (m, 1H), 2.3-2.2 (m, 4H), 2.2-2.1 (m, 4H), 2.0 (s, 3H), 1.7-1.5 (m, 3H), 1.3-1.2 (m, 2H), 1.0 (t, 3H), 0.9 (d, 6H); Anal. (C$_{18}$H$_{28}$O) C, H.

(2Z)-4-(3'-Isopropyl-2'-(3-methylbutyl)-2'-cyclohexen-1'-ylidene))-3-methyl-2-butenal (22)

MS m/z 275 (M+1); $^1$H NMR (300 MHz, CDCl$_3$) δ 9.5 (d, 1H), 6.0 (s, 1H), 5.9 (d, 1H), 3.0-2.9 (m, 1H), 2.3-2.2 (m, 4H), 2.1 (t, 2H), 2.0 (s, 3H), 1.6-1.5 (m, 3H), 1.3-1.2 (m, 2H), 1.00 (d, 6H), 0.9 (d, 6H); $^{13}$C NMR (CDCl$_3$) δ 193.9, 161.5, 146.3, 142.9, 130.4, 128.9, 118.7, 39.4, 30.8, 29.1, 29.0, 25.7, 25.6, 24.8, 23.6, 22.9, 21.1

(2Z)-4-(3'-Cyclopropyl-2'-(3-methylbutyl)-2'-cyclohexen-1'-ylidene))-3-methyl-2-butenal (23)

MS m/z 273 (M+1); $^1$H NMR (300 MHz, CDCl$_3$) δ 9.5 (d, 1H), 6.0 (s, 1H), 5.9 (d, 1H), 2.5-2.4 (m, 2H), 2.2-2.1 (m, 2H), 2.0 (s, 3H), 1.8-1.7 (m, 3H), 1.7-1.5 (m, 3H), 1.4-1.3 (m, 2H), 0.9 (d, 6H), 0.8-0.7 (m, 2H), 0.7-0.6 (m, 2H); $^{13}$C NMR (CDCl$_3$) δ 193.6, 161.1, 142.5, 140.0, 132.8, 128.5, 117.7, 38.3, 28.7, 28.2, 25.9, 25.7, 25.5, 22.9, 22.6, 14.3, 5.0.

(2Z)-4-(2'-(3-Methylbutyl)-3'-phenyl-2'-cyclohexen-1'-ylidene))-3-methyl-2-butenal (24)

MS m/z 309 (M+1); $^1$H NMR (300 MHz, CDCl$_3$) δ 9.6 (d, 1H), 7.4-7.3 (m, 2H), 7.3-7.2 (m, 1H), 7.2-7.1 (m, 2H), 6.1 (s, 1H), 6.0 (d, 1H), 2.4-2.3 (m, 4H), 2.2-2.1 (m, 2H), 2.0 (s, 3H), 1.8-1.7 (m, 2H), 1.4-1.2 (m, 3H), 0.7 (d, 6H); $^{13}$C NMR (CDCl$_3$) δ 193.8, 160.9, 144.4, 142.2, 141.9, 133.8, 129.2, 128.6, 127.9, 127.0, 120.6, 39.4, 34.3, 28.8, 28.5, 27.4, 25.7, 23.7, 22.7.

Horner-Emmons reaction to provide esters 25-28 (FIG. 3): Using the following general procedure, all of the esters were prepared.

(2E,4E,6Z)- and (2Z,4E,6Z)-Ethyl 8-(3'-Ethyl-2'-(3-methylbutyl)-2'-cyclohexen-1'-ylidene))-3,7-dimethyl-2,4,6-octatrienoate (25)

60% NaH in mineral oil (4.96 g, 124 mmol) in a dry three-neck round bottomed flask was suspended in anhydrous THF (600 mL). Freshly distilled triethylphosphonosenecioate (32.75 g, 124.0 mmol) was added. After 15 min of stirring HMPA (87 mL) was added. After another 15 min stirring the aldehyde 21 (21.5 g, 82.7 mmol) in THF (250 mL) was added dropwise. The reaction mixture was stirred for an additional 1.5 hours, quenched with water (200 mL) and diluted with ether (600 mL). The organic layer was separated and the aqueous layer was extracted with ether (2×300 mL). The combined organic layers were washed with brine (2×250 mL), dried (Na$_2$SO$_4$) and concentrated under vacuum to give a crude oil. This was purified by chromatography (silica gel; hexanes/ether 8:1) to give 30.0 g (98.0%) of 25 as an oil (mixture of 9Z and 9Z,13Z isomers in a ratio of 85:15). MS m/z 371 (M+1); $^1$H NMR (300 MHz, CDCl$_3$) δ 6.6 (dd, 1H), 6.2 (d, 1H), 6.02 (d, 1H), 5.9 (s, 1H), 5.7 (s, 1H), 4.1 (q, 2H), 2.3-2.2 (m, 2H), 2.2 (s, 3H), 2.2-2.1 (m, 6H), 1.9 (s, 3H), 1.7-1.5 (m, 3H), 1.4-1.3 (m, 2H), 1.3 (t, 3H), 1.0 (t, 3H), 0.9 (d, 6H); $^{13}$C NMR (CDCl$_3$) δ 167.3, 153.2, 142.0, 140.0, 138.9, 133.4, 133.1, 131.5, 126.7, 120.1, 118.0, 59.5, 39.0, 30.3, 28.7, 28.4, 27.4, 25.6, 24.8, 23.4, 22.6, 14.4, 13.7, 12.9; Anal. (C$_{25}$H$_{38}$O$_2$) C, H.

(2E,4E,6Z)- and (2Z,4E,6Z)-Ethyl 8-(3'-Isopropyl-2'-(3-methylbutyl)-2'-cyclohexen-1'-ylidene))-3,7-dimethyl-2,4,6-octatrienoate (26)

MS m/z 385 (M+1); $^1$H NMR (300 MHz, CDCl$_3$) δ 6.6 (dd, 1H), 6.2 (d, 1H), 6.02 (d, 1H), 5.9 (s, 1H), 5.7 (s, 1H), 4.1 (q, 2H), 3.0-2.9 (m, 1H), 2.3-2.2 (m, 2H), 2.2 (s, 3H), 2.15 (t, 3H), 2.0 (t, 3H), 1.9 (s, 3H), 1.6-1.5 (m, 3H), 1.3-1.2 (m, 5H), 1.0 (d, 6H), 0.9 (d, 6H); $^{13}$C NMR (CDCl$_3$) δ 167.6, 153.5, 143.9, 142.4, 139.5, 133.7, 133.5, 130.9, 127.1, 120.6, 118.4, 59.9, 39.6, 30.7, 29.1, 29.0, 25.8, 25.2, 24.8, 23.8, 23.0, 21.2, 14.7, 14.2.

(2E,4E,6Z)- and (2Z,4E,6Z)-Ethyl 8-(3'-Cyclopropyl-2'-(3-methylbutyl)-2'-cyclohexen-1'-ylidene))-3,7-dimethyl-2,4,6-octatrienoate (27)

MS m/z 383 (M+1); $^1$H NMR (300 MHz, CDCl$_3$) δ 6.6 (dd, 1H), 6.18 (d, 1H), 6.02 (d, 1H), 5.9 (s, 1H), 5.7 (s, 1H), 4.1 (q, 2H), 2.5-2.4 (m, 2H), 2.2 (s, 3H), 2.1 (t, 2H), 1.9 (s, 3H), 1.8-1.7 (m, 3H), 1.7-1.5 (m, 3H), 1.4-1.3 (m, 2H), 1.3 (t, 3H), 0.9 (d, 6H), 0.7-0.6 (m, 2H), 0.6-0.5 (m, 2H); $^{13}$C NMR (CDCl$_3$) δ 167.6, 153.5, 142.4, 139.3, 137.7, 133.8, 133.5, 127.1, 120.0, 118.4, 59.9, 38.9, 29.1, 28.6, 26.3, 26.1, 25.2, 23.4, 23.0, 14.8, 14.6, 14.2, 5.2.

(2E,4E,6Z)- and (2Z,4E,6Z)-Ethyl 8-(2'-(3-Methylbutyl)-3'-phenyl-2'-cyclohexen-1'-ylidene))-3,7-dimethyl-2,4,6-octatrienoate (28)

MS m/z 419 (M+1); $^1$H NMR (300 MHz, CDCl$_3$) δ 7.4-7.3 (m, 2H), 7.3-7.2 (m, 1H), 7.2-7.1 (m, 2H), 6.7 (dd, 1H), 6.2 (d, 1H), 6.08 (d, 1H), 6.0 (s, 1H), 5.7 (s, 1H), 4.18 (q, 2H), 2.4 (t, 2H), 2.3 (s, 3H), 2.3-2.2 (m, 2H), 2.2-2.1 (m, 2H), 1.95 (s, 3H), 1.8-1.7 (m, 2H), 1.4-1.2 (m, 3H), 1.2 (t, 3H), 0.7 (d, 6H); $^{13}$C NMR (CDCl$_3$) δ 167.6, 153.4, 144.9, 141.8, 140.0, 138.5, 134.4, 133.9, 133.5, 128.5, 128.2, 127.5, 126.7, 122.6, 118.6, 60.0, 39.6, 34.3, 28.8, 28.6, 27.5, 25.1, 23.9, 22.8, 14.8, 14.2. General procedure for hydrolysis of the esters 25-28 to provide final products 1-4 (FIG. 3): Using the following general procedure, all of the final acids were prepared.

(2E,4E,6Z)-8-(3'-Ethyl-2'-(3-methylbutyl)-2'-cyclohexen-1'-ylidene))-3,7-dimethyl-2,4,6-octatrienoic Acid (1)

A suspension of ester 25 (30.0 g, 81.1 mmol) in methanol (1300 mL) was treated with KOH (2.5 N, 325 mL) solution. The resulting solution was stirred at reflux for 1 hour, cooled to 0° C. and diluted with ice cold water (500 mL). The mixture was acidified slowly with ice cold 1N HCl to pH 2.5. The resulting yellow precipitate was filtered and washed with ice-cold water. The wet precipitate was dissolved in ether (1000 mL), washed with brine (2×200 mL), dried (Na$_2$SO$_4$) and concentrated to about 100 mL volume under vacuum. The mixture was diluted with hexanes (200 mL) and cooled in the freezer for 18 hours. The resulting yellow crystalline solid was filtered, washed with ice-cold hexanes and dried to give 16.5 g (59.5%) of pure 1 as single 9Z isomer: mp 119-120° C.; MS m/z 342 (M+1); UV λ$_{max}$ 318 nm (E 25 550); $^1$H NMR (300 MHz, CDCl$_3$) δ 6.6 (dd, 1H), 6.2 (d, 1H), 6.04 (d, 1H), 5.9 (s, 1H), 5.7 (s, 1H), 2.3-2.2 (m, 2H), 2.2 (s, 3H), 2.2-2.1 (m, 6H), 1.9 (s, 3H), 1.6-1.5 (m, 3H), 1.4-1.3 (m, 2H), 1.0 (t, 3H), 0.9 (d, 6H); $^{13}$C NMR (CDCl$_3$) δ 172.7, 155.8, 142.9, 140.2, 139.1, 134.4, 132.9, 131.4, 126.7, 120.1, 117.1, 39.0, 30.3, 28.7, 28.4, 27.4, 25.6, 24.9, 23.4, 22.6, 13.9, 12.9; Anal. (C$_{23}$H$_{34}$O$_2$) C, H.

(2E,4E,6Z)-8-(3'-Isopropyl-2'-(3-methylbutyl)-2'-cyclohexen-1'-ylidene))-3,7-dimethyl-2,4,6-octatrienoic Acid (2)

mp 169-170° C.; MS m/z 356 (M+1); UV λ$_{max}$ 328 nm (ε 25 900); $^1$H NMR (300 MHz, CDCl$_3$) δ 6.6 (dd, 1H), 6.2 (d, 1H), 6.04 (d, 1H), 5.9 (s, 1H), 5.7 (s, 1H), 3.0-2.9 (m, 1H), 2.3-2.2 (m, 2H), 2.2 (s, 3H), 2.1 (t, 2H), 2.0 (t, 2H), 1.9 (s, 3H), 1.6-1.5 (m, 3H), 1.3-1.2 (m, 2H), 1.0 (d, 6H), 0.9 (d, 6H); $^{13}$C NMR (CDCl$_3$) δ 173.2, 156.2, 144.1, 143.4, 139.8, 134.7, 133.3, 130.9, 127.1, 120.6, 117.6, 39.6, 30.7, 29.1, 29.0, 25.8, 25.3, 24.8, 23.8, 23.0, 21.2, 14.4.

(2E,4E,6Z)-8-(3'-Cyclopropyl-2'-(3-methylbutyl)-2'-cyclohexen-1'-ylidene))-3,7-dimethyl-2,4,6-octatrienoic Acid (3)

mp 160-162° C.; MS m/z 355 (M+1); UV λ$_{max}$ 326 nm (ε 22 300); $^1$H NMR (300 MHz, CDCl$_3$) δ 6.65 (dd, 1H), 6.2 (d, 1H), 6.04 (d, 1H), 5.9 (s, 1H), 5.7 (s, 1H), 2.5-2.4 (m, 2H), 2.2 (s, 3H), 2.15 (t, 2H), 1.9 (s, 3H), 1.8-1.7 (m, 3H), 1.7-1.5 (m, 3H), 1.4-1.3 (m, 2H), 0.9 (d, 6H), 0.7-0.6 (m, 2H), 0.6-0.5 (m2H); $^{13}$C NMR (CDCl$_3$) δ 173.2, 156.2, 143.3, 139.5, 137.8, 134.8, 133.8, 133.3, 127.1, 120.0, 117.6, 38.9, 29.1, 28.7, 26.4, 26.1, 25.3, 23.4, 23.1, 14.6, 14.4, 5.2.

(2E,4E,6Z)-8-(2'-(3-Methylbutyl)-3'-phenyl-2'-cyclohexen-1'-ylidene))-3,7-dimethyl-2,4,6-octatrienoic Acid (4)

mp 168-169° C.; MS m/z 391 (M+1); UV λ$_{max}$ 328 nm (ε 26 300); $^1$H NMR (300 MHz, CDCl$_3$) δ 7.4-7.3 (m, 2H), 7.3-7.2 (m, 1H), 7.2-7.1 (m, 2H), 6.7 (dd, 1H), 6.24 (d, 1H), 6.1 (d, 1H), 6.0 (s, 1H), 5.8 (s, 1H), 2.4 (t, 2H), 2.3 (s, 3H), 2.3-2.2 (m, 2H), 2.2-2.1 (m, 2H), 1.97 (s, 3H), 1.8-1.7 (m, 2H), 1.4-1.3 (m, 3H), 0.7 (d, 6H); $^{13}$C NMR (CDCl$_3$) δ 173.1, 156.1, 144.9, 142.7, 140.1, 138.7, 134.5, 134.4, 133.7, 128.5, 128.2, 127.5, 126.8, 122.5, 117.8, 39.6, 34.3, 28.8, 28.6, 27.6, 25.2, 23.9, 22.8, 14.5.

III. Reduction of Serum Triglycerides (2E,4E,6E,8E)-8-(3',4'-dihydro-8'-methyl-1'(2'H-naphthalen-1'-ylidene))-3,7-dimethyl-2,4,6-octatrienoic acid and (2E,4E,6Z)-8-(3'-cyclopropyl-2'-(3-methylbutyl)-2'-cyclohexen-1'-ylidene))-3,7-dimethyl-2,4,6-octatrienoic acid decreased serum triglycerides by 70% (79 mg/dL) and by 33% (171 mg/dL), respectively, in the serum of female rats after 3 hours relative to the corn oil vehicle (256 mg/dL).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES (1) Rosen, J., et al., J. Med. Chem. 38: 4855-4874. (1995)
(2) (a) Mangelsdorf, D. J., et al., In the Retinoids Biology, Chemistry and Medicine; 2nd ed., Raven Press: New York. pp. 319-349. (1994) (b) Gudas, L., J. Biol. Chem. 269: 15399-15402. (1994)
(3) Nadzan, A. M., Annu Rev. Med. Chem. 30:119-128. (1995)
(4) Degos, L., et al., Blood 85:2643-2653. (1995)
(5) Caetleberry, R. P., et al., N. Engl. J. Med. 331:1680-1684. (1994)
(6) Emanuel, P. D., et al., Mol. Med. Today 2: 468-475. (1996)
(7) Muccio, D. D., et al., U.S. Pat. No. 5,094,783, Mar. 10, 1992.
(8) Muccio, D. D., et al., J. Med. Chem. 39: 3625-3635. (1996)
(9) Alam, M., et al., J. Med. Chem. 38: 2303-2310. (1995)
(10) Vaezi, M. F., et al., J. Med. Chem. 37: 4499-4507. (1994)
(11) Vaezi, M. F., et al., Org. Prep. Proc. Int. 19: 187-195. (1987)
(12) Hale, et al., Labeled Compds. Radiopharm. 13: 123-135 (1977)
(13) Zhang, X.-K., Nature 355: 441-446. (1992)
(14) Verma, A., et al., Cancer Res. 37: 2196-2201. (1977)
(15) (a) Breitman, T. R., et al., Methods Enzymol. 190: 118-130. (1990). (b) Tiami, M., et al., Exp. Cell Res. 230: 69-75. (1997)
(16) (a) Emanuel, P. D., et al., Exp. Hematol. 19: 1017-1024. (1991). (b) Emanuel, P. D., et al., Blood 77: 925-929. (1991)
(17) Lake, C. H., et al., J. Chem. Crystallogr 27: 231-235. (1997)
(18) (a) Sani, B. P., et al., Biochem. J. 171: 711-717. (1978). (b) Sani, B. P., In Chemistry and Biology of Synthetic Retinoids; Dawson, M. I., Okamuar, W. H., Eds.; CRC Press: Boca Raton, Fla., pp 365-384. (1990)
(19) Graupner, G., et al., Nature (London) 340: 653-656. (1989)
(20) (a) Chandraratna, R. A. S., et al., BioMed. Chem. Lett. 5: 523-527. (1995). (b) Nagpal, S., et al., J. Biol. Chem. 270: 923-927. (1995)
(21) Castleberry, R. P., et al., Blood 78 (Suppl. 1), 170a. (1991)
(22) (a) Lapidot, T., et al., Blood 82 (Suppl. 1), 197a. (1993). (b) Cambier, N., et al., Blood 86 (Suppl. 1), 791a. 91995)
(23) Emanuel, P. D., et al., Blood (Suppl. 1), 728a. (1995)
(24) (a) Yang Yen, H.-F., et al., New Biol. 3: 1206-1219. (1991)
(25) Salbert, G., et al., Mol. Endocrinol. 7: 1347-1356. (1993)
(26) (a) Fanjul, A., et al., Nature 372: 107-111. (1994). (b) Nagpal, S., J. Biol. Chem. 270: 923-927. (1995)
(27) (a) Kizaki, M., et al., Blood 83: 3289-3297. (1994). (b) Kizaki, M., et al., Blood 87: 1977-1984. (1996)
(28) Chen, J.-Y., Nature 382: 819-822. (1996)
(29) Lin, T.-H., et al., Toxicol. Appl. Pharmacol. 139: 310-316. (1996)
(30) M. A. Anzano, W. W. Byers, J. M. Smith, C. W. Peer, L. T. Mullen, C. C. Brown, A. B. Roberts, M. B. Sporn, Prevention of breast cancer in the rat with 9-cis-retinoic acid as a single agent and in combination with tamoxifen. Cancer Res. 54 (1994) 4614-4617.
(31) V. A. Miller, J. R. Rigas, F. M. Benedetti, A. L. Verret, W. P. Tong, M. G. Kris, G. M. Gill, G. R. Loewen, J. A. Truglia, E. H. Ulm, R. P. Warrell, Jr, Initial clinical trial of the retinoid receptor pan agonist 9-cis retinoic acid. Clin. Cancer Res. 2 (1996) 471-475.
(32) J. S. Lee, R. A. Newman, S. M. Lippman, M. H. Huber, T. Minor, M. N. Raber, I. H. Krakoff, W. K. Hong, Phase 1 evaluation of all-trans-retinoic acid in adults with solid tumors. J. Clin. Oncol. 11 (1993) 959-966.
(33) J. K. Jonathan, R. Lotan, J. J. Lee, J. S. Lee, R. C. Morice, D. D. Liu, X-C. XU, F. R. Khuri, J. Y. Ro, W. H. Hittelman, G. L. Walsh, J. A. Roth, J. D. Minna, W. K. Hong, Treatment of former smokers with 9-cis-retinoic acid reverse loss of retinoic acid receptor-β expression in the bronchial epithelium: results from a randomized placebo-controlled trial. J. Natl. Cancer Inst. 95: (2003) 206-214.
(34) J. M. Lehmann, L. Jong, A. Fanjul, J. F. Cameron, X. P. Lu, P. Haefner, M. A. Dawson, M. Pfahl, Retinoids selective for retinoid x receptor response pathways, Science (1992) 1944-1946.
(35) M. F. Boehm, L. Zhang, B. A. Badea, S. K. White, D. E. Mais, E. Berger, C. M. Suto, M. E. Goldman, R. A. Heyman, Synthesis and structure-activity relationships of novel X receptor-selective retinoids. J. Med. Chem. 37 (1994) 2930-2941.
(36) M. F. Vaezi, M. Alam, B. P. Sani, T. S. Rogers, L. Simpson-Herren, J. J. Wille, D. L. Hill, T. I Doran, W. J. Brouillette, D. D. Muccio, A conformationally defined 6-s-trans retinoic acid isomer: synthesis, chemopreventive activity and toxicity. J. Med. Chem. 37 (1994) 4499-4507.
(37) D. D. Muccio, W. J. Brouillette, T. R. Breitman, M. Taimi, P. D. Emanuel, X. Zhang, G. Chen, B. P. Sani, P. Venepally, L. Reddy, M. Alam, L. Simpson-Herren, D. L. Hill. Conformationally defined retinoic acid analogues. 4. Potential new agents for acute promyelocytic and juvenile myelomonocytic leukemias. J. Med. Chem. 41 (1998) 1679-1687.
(38) N. Suh, A. L. Glasebrook, A. D. Palkowitz, H. V. Bryant, L. L. Burris, J. J. Starling, H. L. Pearce, C. Williams, C. Peer, Y. Wang, and M. B. Sporn. Arzoxifene, a new selective estrogen receptor modulator for chemoprevention of experimental breast cancer. Cancer Res. 61 (2001) 8412-8415.

What is claimed is:

1. A compound having the formula XXX

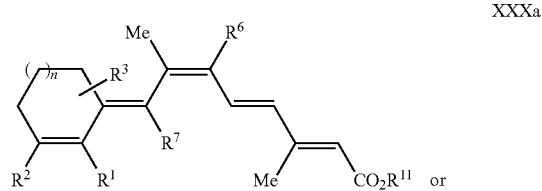

XXXa or

-continued

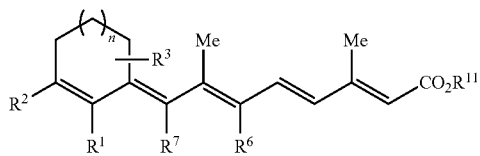

XXXb wherein $R^1$ is a $C_5$-$C_{15}$ branched or straight chain alkyl group;

$R^2$ is hydrogen, a $C_1$-$C_{15}$ branched or straight chain alkyl group, an aryl group, an aralkyl group, or a cycloalkyl group; and $R^3$ is one or more groups independently selected from the group consisting of hydrogen, a $C_1$-$C_{15}$ branched or straight chain alkyl group, an aryl group, an aralkyl group, and a cycloalkyl group;

$R^6$ and $R^7$ are, independently, hydrogen, a $C_1$-$C_{15}$ branched or straight chain alkyl group, or a cycloalkyl group;

$R^{11}$ is hydrogen or a $C_1$-$C_{15}$ branched or straight chain alkyl group; and n is from 0 to 3, wherein one or more carbon atoms in the ring in formula XXX can optionally be replaced with a heteroatom, or the pharmaceutically-acceptable salt or ester thereof.

2. The compound of claim 1, wherein n is 1.

3. The compound of claim 1, wherein $R^3$ is hydrogen.

4. The compound of claim 1, wherein $R^6$, $R^7$, and $R^{11}$ are hydrogen.

5. The compound of claim 1, wherein n is 1, and $R^2$ is a $C_1$-$C_{15}$ branched or straight chain alkyl group.

6. The compound of claim 1, wherein n is 1, and $R^1$ is pentyl, isopentyl, neopentyl, hexyl, heptyl, octyl, nonyl, or decyl.

7. The compound of claim 1, wherein $R^1$ is an isopentyl group; $R^2$ is methyl, ethyl, propyl, isopropyl, butyl, isobutyl, phenyl, cyclopropyl, cyclobutyl, cyclopentyl, cyclohexyl, or benzyl; and $R^6$, $R^7$, and $R^{11}$ are hydrogen.

8. A compound having the formula XXXII

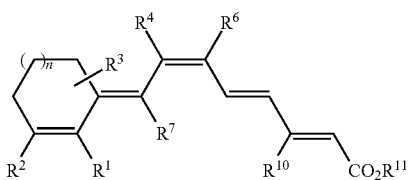

XXXIIa

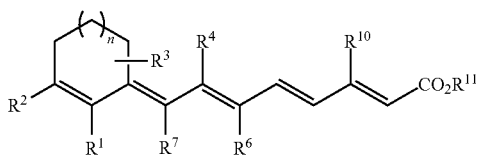

XXXIIb wherein $R^1$ and $R^2$ are independently selected from the group consisting of hydrogen, a $C_1$-$C_{15}$ branched or straight chain alkyl group, an aryl group, an aralkyl group, and a cycloalkyl group, or $R^1$ and $R^2$ collectively form a fused aryl group;

$R^3$ is one or more groups independently selected from the group consisting of hydrogen, a $C_1$-$C_{15}$ branched or straight chain alkyl group, an aryl group, an aralkyl group, and a cycloalkyl group;

$R^4$, $R^6$, and $R^7$ are, independently, hydrogen, a $C_1$-$C_{15}$ branched or straight chain alkyl group, or a cycloalkyl group;

$R^{10}$ and $R^{11}$ are, independently, hydrogen or a $C_1$-$C_{15}$ branched or straight chain alkyl group; and n is from 0 to 3, wherein one or more carbon atoms in the ring in formula XXXII can optionally be replaced with a heteroatom, or the pharmaceutically-acceptable salt or ester thereof, wherein $R^4$ and $R^{10}$ are not both a methyl group.

9. A pharmaceutical composition comprising the compound of claim 1 and a pharmaceutically-acceptable carrier.

10. A pharmaceutical composition comprising the compound of claim 8 and a pharmaceutically-acceptable carrier.

11. The compound of claim 1, wherein $R^1$ is isopentyl.

* * * * *

UNITED STATES PATENT AND TRADEMARK OFFICE
CERTIFICATE OF CORRECTION

PATENT NO. : 9,169,190 B2
APPLICATION NO. : 13/856631
DATED : October 27, 2015
INVENTOR(S) : Wayne J. Brouillette et al.

It is certified that error appears in the above-identified patent and that said Letters Patent is hereby corrected as shown below:

In the Specification

Column 1, Lines 14-17, Delete:
"The research leading to this invention was funded in part by the National Institutes of Health, Grant No. 5P50CA89019. The U.S. Government may have certain rights in this invention."

And Insert:
-- This invention was made with government support under CA089019 awarded by the National Institutes of Health. The government has certain rights in the invention. --

Signed and Sealed this
Twenty-eighth Day of November, 2023

Katherine Kelly Vidal
*Director of the United States Patent and Trademark Office*